United States Patent [19]

Goodman et al.

[11] Patent Number: 5,808,146
[45] Date of Patent: Sep. 15, 1998

[54] AMINO ACID ANALOGS FOR TUMOR IMAGING

[75] Inventors: Mark M. Goodman, Atlanta; Timothy Shoup, Decatur, both of Ga.

[73] Assignee: Emory University, Atlanta, Ga.

[21] Appl. No.: 554,906

[22] Filed: Nov. 9, 1995

[51] Int. Cl.$^6$ .................................................. C07C 61/06
[52] U.S. Cl. ......................... 562/504; 562/505; 562/507; 562/574
[58] Field of Search ................................... 562/505, 504, 562/507, 574

[56] References Cited

U.S. PATENT DOCUMENTS

| | | | |
|---|---|---|---|
| 4,325,961 | 4/1982 | Kollonitsch et al. | |
| 4,483,870 | 11/1984 | Kollonitsch | 424/309 |
| 4,695,588 | 9/1987 | Kollonitsch | 514/538 |
| 5,227,467 | 7/1993 | Durette | 530/321 |

OTHER PUBLICATIONS

DiChiro, G. et al. (1982) *Neurology* (NY) 32:1323–1329.
Washburn, L.C. et al. (1979) *J. Nucl. Med.* 20:1055–1061.
Washburn, L.C. et al. in *Radiopharmaceuticals II: Proceedings 2nd International Symposium on Radiopharmaceuticals*, Mar. 19–22, 1979, Seattle, Washington.
Bey, J. Org. Chem., vol. 44, pp. 2732–2742, 1979.
Finar, "Organic Chemistry, vol. 1, The Fundmental Principles," 6th Ed., pp. 61–62, 1973.

*Primary Examiner*—Michael L. Shippen
*Attorney, Agent, or Firm*—Greenlee Winner and Sullivan

[57] ABSTRACT

The invention provides novel amino acid compounds of use in detecting and evaluating brain and body tumors. These compounds combine the advantageous properties of 1-amino-cycloalkyl-1-carboxylic acids, namely, their rapid uptake and prolonged retention in tumors with the properties of halogen substituents, including certain useful halogen isotopes including fluorine-18, iodine-123, iodine-125, iodine-131, bromine-75, bromine-76, bromine-77 and bromine-82.

In one aspect, the invention features amino acid compounds that have a high specificity for target sites when administered to a subject in vivo. Preferred amino acid compounds show a target to non-target ratio of at least 5:1, are stable in vivo and substantially localized to target within 1 hour after administration. An especially preferred amino acid compound is [$^{18}$F]-1-amino-3-fluorocyclobutane-1-carboxylic acid (FACBC).

In another aspect, the invention features pharmaceutical compositions comprised of an α-amino acid moiety attached to either a four, five, or a six member carbon-chain ring. In addition, the invention features analogs of α-aminoisobutyric acid.

27 Claims, No Drawings

AMINO ACID ANALOGS FOR TUMOR IMAGING

The U.S. Government has certain rights in this invention, based upon partial support provided by Department of Energy Grant No. DE-FG05-93ER61737.

FIELD OF THE INVENTION

The invention includes novel chemical compounds having specific binding in a biological system and capable of being used for positron emission tomography (PET) and single photon emission (SPECT) imaging methods.

BACKGROUND OF THE INVENTION

The ability of analog compounds to bind to localized ligands within the body would make it possible, in principle, to utilize such compounds for in situ imaging of the ligands by PET, SPECT and similar imaging methods. In principle, nothing need be known about the nature of the ligand, as long as binding occurs, and such binding is specific for a class of cells, organs, tissues or receptors of interest. PET imaging is accomplished with the aid of tracer compounds labeled with a positron-emitting isotope (Goodman, M. M. *Clinical Positron Emission Tomography*, Mosby Yearbook, 1992, K. F. Hubner et al., Chapter 14). For most biological materials, suitable isotopes are few. The carbon isotope, [$^{11}$C], has been used for PET, but its short half-life of 20.5 minutes limits its usefulness to compounds that can be synthesized and purified quickly, and to facilities that are proximate to a cyclotron where the precursor [$^{11}$C] starting material is generated. Other isotopes have even shorter half-lives. [$^{13}$N] has a half-life of 10 minutes and [$^{15}$O] has an even shorter half-life of 2 minutes. The emissions of both are more energetic than those of [$^{11}$C]. Nevertheless, PET studies have been carried out with these isotopes (Hubner, K. F., in *Clinical Positron Emission Tomography*, Mosby Year Book, 1992, K. F. Hubner, et al., Chapter 2). A more useful isotope, [$^{18}$F], has a half-life of 110 minutes. This allows sufficient time for incorporation into a radio-labeled tracer, for purification and for administration into a human or animal subject. In addition, facilities more remote from a cyclotron, up to about a 200 mile radius, can make use of [$^{18}$F] labeled compounds. Disadvantages of [$^{18}$F] are the relative scarcity of fluorinated analogs that have functional equivalence to naturally-occurring biological materials, and the difficulty of designing methods of synthesis that efficiently utilize the starting material generated in the cyclotron. Such starting material can be either fluoride ion or fluorine gas. In the latter case only one fluorine atom of the bimolecular gas is actually a radionuclide, so the gas is designated $^{18}$F-F. Reactions using $^{18}$F-F as starting material therefore yield products having only one half the radionuclide abundance of reactions utilizing K$^{18}$F as starting material. On the other hand, [$^{18}$F] can be prepared in curie quantities as fluoride ion for incorporation into a radiopharmaceutical compound in high specific activity, theoretically 1.7 Ci/nmol using carrier-free nucleophilic substitution reactions. The energy emission of [$^{18}$F] is 0.635 MeV, resulting in a relatively short, 2.4 mm average positron range in tissue, permitting high resolution PET images.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is [$^{123}$I], a γ-emitter with a 13.3 hour half life. Compounds labeled with [$^{123}$I] can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Use of [$^{18}$F] labeled compounds in PET has been limited to a few analog compounds. Most notably, [$^{18}$F]-fluorodeoxyglucose has been widely used in studies of glucose metabolism and localization of glucose uptake associated with brain activity. [$^{18}$F]-L-fluorodopa and other dopamine receptor analogs have also been used in mapping dopamine receptor distribution.

Other halogen isotopes can serve for PET or SPECT imaging, or for conventional tracer labelling. These include $^{75}$Br, $^{76}$Br, $^{77}$Br and $^{82}$Br as having usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homologs.

Numerous studies have demonstrated increased incorporation of carbohydrates and amino acids into malignant tumor cells. This accumulation is associated with accelerated proliferation and protein synthesis of such cells. The glucose analog [$^{18}$F]-2-fluoro-2-deoxy-D-glucose (2-FDG) has been used for distinguishing highly malignant brain tumors from normal brain tissue or benign growths (DiChiro, G. et al. (1982) *Neurology* (NY) 32:1323–1329. However, fluorine-18 labeled 2-FDG is not the agent of choice for detecting low grade brain tumors because high uptake in normal tissue can mask the presence of a tumor. In addition, fluorine-18 labeled 2-FDG is not the ideal radiopharmaceutical for distinguishing lung tumors from infectious tissue or detecting ovarian carcinoma because of high uptake of the 2-FDG radioactivity in infectious tissue and in the bladder, respectively. The naturally occurring amino acid methionine, labeled with carbon-11, has also been used to distinguish malignant tissue from normal tissue. But it too has relatively high uptake in normal tissue. Moreover, the half-life of carbon-11 is only 20 minutes, therefore [$^{11}$C] methionine can not be stored for a long period of time.

In an article titled, "1-Aminocyclobutane[$^{11}$C] carboxylic Acid, a Potential Tumor-Seeking Agent," published in *J. Nucl. Med.*20:1055–1061 (1979), L. C. Washburn et al. reported that the unnatural, alicyclic α-amino acid, 1-aminocyclobutanecarboxylic acid (ACBC), labeled with carbon-14 or carbon-11, was incorporated preferentially by several tumor types in animals. ACBC has been shown to be a selective substrate for protein synthesis in metastatic lesions in the brain with little observable uptake in normal brain tissue.

1-Amino-1-cyclobutane carboxylic acid is also a selective and potent ligand and antagonist for the excitatory amino acid receptor subtype N-methyl-D-aspartic acid (NMDA), specifically the strychnine-insensitive glycine recognition site. The NMDA receptor has been implicated in CNS disorders such as epilepsy, stroke, Huntington's disease, Alzheimer's disease and schizophrenia.

Synthesis of ACBC has been carried out by the well-known Bücherer-Streker synthesis which is suitable for labeling with [$^{11}$C] using [$^{11}$C]-cyanide as precursor. (Washburn, L. C. et al., in *Radiopharmaceuticals II: Proceedings 2nd International Symposium on Radiopharmaceuticals*, Mar. 19–22, 1979, Seattle, Wash.)

SUMMARY OF THE INVENTION

The invention provides novel amino acid compounds of use in detecting and evaluating brain and body tumors. These compounds combine the advantageous properties of 1-amino-cycloalkyl-1-carboxylic acids, namely, their rapid uptake and prolonged retention in tumors with the properties of halogen substituents, including certain useful halogen isotopes including fluorine-18, iodine-123, iodine-125, iodine-131, bromine-75, bromine-76, bromine-77 and bromine-82.

In one aspect, the invention features amino acid compounds that have a high specificity for target sites when administered to a subject in vivo. Preferred amino acid compounds show a target to non-target ratio of at least 5:1, are stable in vivo and substantially localized to target within 1 hour after administration. An especially preferred amino acid compound is [$^{18}$F]-1-amino-3-fluorocyclobutane-1-carboxylic acid (FACBC).

In another aspect, the invention features pharmaceutical compositions comprised of an α-amino acid moiety attached to either a four, five, or a six member carbon-chain ring. In addition, the invention features analogs of α-aminoisobutyric acid.

In a further aspect, the invention features amino acid compounds further comprising an imaging agent and uses for the compounds in detecting and/or monitoring tumors in a subject. In one embodiment, the amino acid compound imaging agent is administered in vivo and monitored using a means appropriate for the label. Preferred methods for detecting and/or monitoring an amino acid compound imaging agent in vivo include Positron Emission Tomography (PET) and Single Photon Emission Computer Tomography (SPECT).

Compounds of the invention include fluoro-, bromo- or iodo-substituted cyclobutyl, cyclopentyl, cyclohexyl amino acids as shown in Scheme 1 or singly unsaturated cyclic homologs thereof as shown in Scheme 2, or methylenyl fluoride or iodide-substituted analogs, as shown in Scheme 3, or fluoro- or iodo-substituted isobutyl amino acids as shown in Scheme 4. The substituted cyclic compounds of Schemes 1–3 belong to the following generic formula:

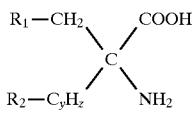

where $R_1$ is X, X—CH=CH—, or $R_3$
$R_2$ is H, or $R_3$ if $R_1$ is $R_3$,

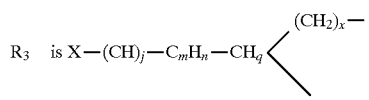

such that

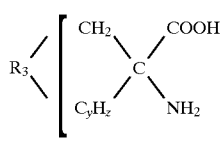

is formed
where x is 0 or 1,
y is 1 or 2, z is 1, 2, 3 or 4 and z>y if y is 2,
q is 1 or 0 if n is 1 and j is 0,
n is 1 or 2, but 0 if m is 0,
m is 0 or 1,
j is 0 or 1, and
X is F, $^{18}$F, I, $^{123}$I, $^{125}$I, $^{131}$I, Br, $^{75}$Br, $^{76}$Br, $^{77}$Br, or $^{82}$Br.

Non-cyclic, but sterically similar compounds of the invention have the following generic formula, as shown in Scheme 4.

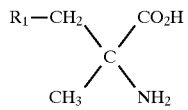

where $R_1$ is X or X—CH=CH—
and x is I, $^{131}$I, $^{123}$I, $^{125}$I, F, $^{18}$F, Br, $^{75}$Br, $^{76}$Br, $^{77}$Br or $^{82}$Br.

The compounds of the invention are useful as tumor-binding agents and as NMDA receptor-binding ligands, and in radio-isotopic form are especially useful as tracer compounds for tumor imaging techniques, including PET and SPECT imaging. In order to synthesize the compounds to maximize a useful lifetime for short-lived isotopes, and to maximize yield and purity, specialized, non-standard routes had to be devised, as described.

SCHEME 1

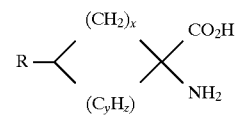

R = $^{75}$Br, $^{76}$Br, $^{77}$Br, $^{82}$Br     x = 1 or 2
$^{131}$I, $^{123}$I, $^{125}$I, $^{18}$F, $^{18}$FCH$_2$     y = 1 or 2
    z = 2 or 4

$^{18}$F—HC=CH—     $^{125}$I—HC=CH—

SCHEME 2

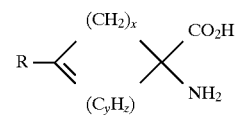

R = $^{75}$Br, $^{76}$Br, $^{77}$Br, $^{82}$Br,     x = 1 or 2
$^{123}$I, $^{125}$I, $^{131}$I     y = 1 or 2
    z = 1 or 3

SCHEME 3

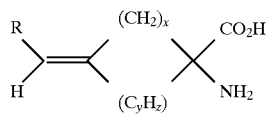

R = $^{123}$I, $^{125}$I, $^{131}$I, $^{18}$F,     x = 1 or 2
$^{75}$Br, $^{76}$Br, $^{77}$Br, $^{82}$Br     y = 1 or 2
    z = 2 or 4

SCHEME 4

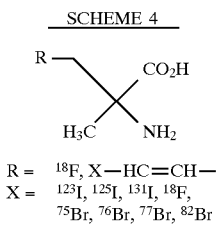

R = ¹⁸F, X—HC=CH—
X = ¹²³I, ¹²⁵I, ¹³¹I, ¹⁸F,
⁷⁵Br, ⁷⁶Br, ⁷⁷Br, ⁸²Br

DETAILED DESCRIPTION OF THE INVENTION

Compounds of the invention provide substantially improved PET imaging for areas of the body having malignant tumors, especially tumors of the brain. All the available positron-emitting isotopes which could be incorporated into a biologically-active compound have short half-lives. The practical utility of such labeled compounds is therefore dependent on how rapidly the labeled compound can be synthesized, the synthetic yield and the radiochemical purity of the final product. Even the shipping time from the isotope source, a cyclotron facility, to the hospital or laboratory where PET imaging is to take place, is limited. A rough calculation of the useful distance is about two miles per minute of half-life. Thus [$^{11}$C], with a half-life of 20.5 m is restricted to about a 40 mile radius from a source whereas compounds labeled with [$^{18}$F] can be used within about a 200 mile radius. Further requirements of an [$^{18}$F]-labeled compound are that it have the binding specificity for the receptor or target molecule it is intended to bind, that non-specific binding to other targets be sufficiently low to permit distinguishing between target and non-target binding, and that the label be stable under conditions of the test to avoid exchange with other substances in the test environment. More particularly, compounds of the invention must display adequate binding to the desired target while failing to bind to any comparable degree with other tissues or cells. Furthermore, the fluorine, iodine or bromine label must not be labile or unstable such that significant amounts appear in, e.g. bone or thyroid, or other non-taret tissue respectively.

A partial solution to the stringent requirements for PET imaging is to employ γ-emitting isotopes in SPECT imaging. [$^{123}$I] is a commonly used isotopic marker for SPECT, having a half-life of 13 hours for a useful range of over 1000 miles from the site of synthesis. Compounds of the invention can be rapidly and efficiently labeled with [$^{123}$I] for use in SPECT analysis as an alternative to PET imaging. Furthermore, because of the fact that the same compound can be labeled with either isotope, it is possible for the first time to compare the results obtained by PET and SPECT using the same tracer.

In vivo distribution of a compound of the invention, [$^{18}$F]-1-amino-3-fluoro-cyclobutane-1-carboxylic acid (FACBC) was measured in rats having an implanted gliosarcoma. Accumulation in various tissue was measured at 5 min and 60 min post-administration. The compound was immediately seen to be preferentially associated with tumor tissue as early as 5 minutes post administration, with relatively little uptake in other tissues. After 60 minutes, an increased level of tumor uptake relative to non-malignant brain tissue was observed, with very little additional uptake in other tissues. Uptake by bone was essentially constant over the 60 minutes of exposure, indicating stability of the 2-cyclobutyl group to significant in vivo defluorination. The tumor uptake exhibited a maximum at 60 minutes of 1.72% of total injected dose/gram of tissue, with a maximum ratio of tumor to brain of 6.61, compared to 5.58 at 5 minutes. By contrast, [$^{18}$F] fluorodeoxyglucose (FDG) showed rapid accumulation but poor discrimination between tumor and brain, the dose/gram ratio of tumor uptake to brain uptake being 0.84 at 60 min. The results with [$^{18}$F]FACBC indicate that the compound is a valuable imaging agent for diagnosis, management and imaging of malignant tumors, using PET imaging.

The specificity of tumor binding also provides utility for I-substituted compounds of the invention. Such compounds can be labeled with short-lived $^{123}$I for SPECT imaging or with longer-lived $^{125}$I for longer-term studies such as monitoring a course of therapy. Other iodine and bromine isotopes can be substituted for those exemplified.

The compounds of the invention therefore provide improved methods for tumor imaging using PET and SPECT. The methods entail administering to a subject (which can be human or animal, for experimental and/or diagnostic purposes) an image-generating amount of a compound of the invention, labeled with the appropriate isotope and then measuring the distribution of the compound by PET if [$^{18}$F] or other positron emitter is employed, or SPECT if [$^{123}$I] or other gamma emitter is employed. An image-generating amount is that amount which is at least able to provide an image in a PET or SPECT scanner, taking into account the scanner's detection sensitivity and noise level, the age of the isotope, the body size of the subject and route of administration, all such variables being exemplary of those known and accounted for by calculations and measurements known to those skilled in the art without resort to undue experimentation.

It will be understood that compounds of the invention can be labeled with an isotope of any atom or combination of atoms in the structure. While [$^{18}$F], [$^{123}$I] and [$^{125}$I] have been emphasized herein as being particularly useful for PET, SPECT and tracer analysis, other uses are contemplated including those flowing from physiological or pharmacological properties of stable isotope homologs and will be apparent to those skilled in the art.

EXAMPLE 1

Synthesis of [18F]-1-amino-3-fluoro-cyclobutane-1-carboxylic acid (FACBC)

As will be described in detail hereinafter, the compound can be prepared by the steps represented in Steps 1–11.

The following methods were employed in procedures reported herein. [$^{18}$F]-Fluoride was produced from a Siemens cyclotron using the $^{18}$O(p,n)$^{18}$F reaction with 11 MeV protons on 95% enriched [$^{18}$O] water. All solvents and chemicals were analytical grade and were used without further purification. Melting points of compounds were determined in capillary tubes by using a Buchi SP apparatus. Thin-layer chromatographic analysis (TLC) was performed by using 250-mm thick layers of silica gel G PF-254 coated on aluminum (obtained from Analtech, Inc.). Column chromatography was performed by using 60–200 mesh silica gel (Aldrich Co.). Infrared spectra (IR) were recorded on a Beckman 18A spectrophotometer with NaCl plates. Proton nuclear magnetic

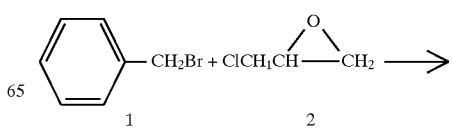

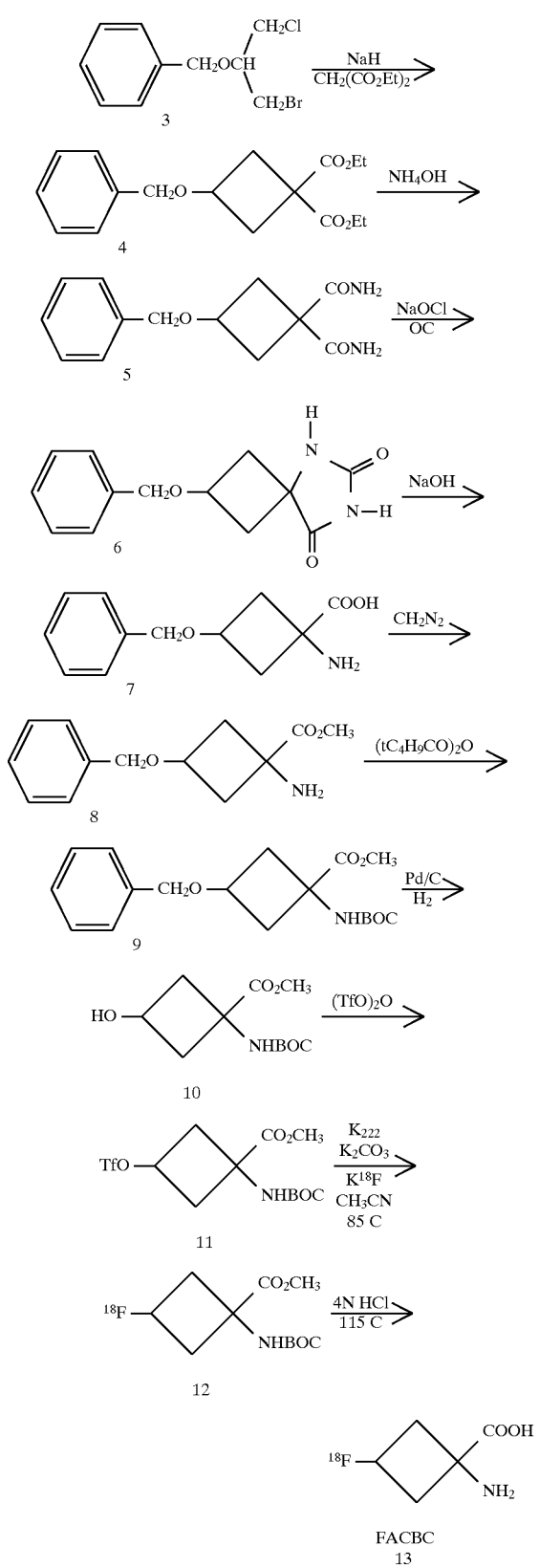

resonance spectra (1H NMR) were obtained at 300 MHz with a Nicolet high-resolution instrument.

Synthesis of 1-Chloro-2-benzyloxy-3-bromopropane 3:

A mixture of benzyl bromide 1 (46.2 g, 0.27 mol), epichlorohydrin 2 (25 g, 0.27 mol), and 0.045 g of mercurous chloride was heated for 12 hr at 150° C. (Step 1). Distillation through a 12-in Vigreux column yielded 55.8 g (79%) of 1-chloro-2-benzyloxy-3-bromopropane, 3 bp 142–145 (0.3 mm); 1H NMR (CDCl$_3$) δ 3.34–3.9 (m, 4H, CH$_2$), 4.58 (s, 2H,O—CH$_2$), 7.26 (s, 5H, phenyl).

Synthesis of Diethyl-3-benzyloxy cyclobutane-1-dicarboxylate 4:

To a stirred slurry of 4.6 g (0.19 mol) sodium hydride in 115 mL of dry dioxane was added dropwise 30.4 (0.10 mol) of diethyl malonate over a 30 min period. After this addition was complete, 50.0 g (0.19 mol) of 1-chloro-2-benzyloxy-3-bromopropane 3 was added dropwise in 30 min (Step 2). The mixture was heated at reflux for 44 hr, cooled to room temperature, and 4.6 g (0.19 mol) of sodium hydride in 50 mL of dioxane was added in portions. The mixture was heated at reflux for an additional 120 hr. The solvent was partially removed under reduced pressure and the mixture was treated with 100 mL of water. The organic layer was extracted into ether. The ether extracts were dried and concentrated and the residue was distilled under reduced pressure. Distillation through a 12-in Vigreux column yielded 49.0 g (85%) of diethyl 3-benzyloxycyclobutane-1,1-dicarboxylate 4 bp 174°–176° C. (0.9 mm); $^1$H NMR (CDCl$_3$) δ 1.23 (t, J=7 Hz, 6H, CH$_3$), 4.0–4.7 (m, 1H OCH), 4.34 (s, 2H OCH$_2$), 4.13 (q, J=7 Hz, 4H, OCOCH$_2$), 7.23 (s, 5H, phenyl).

Synthesis of 3-benzyloxycyclobutane-1,1-dicarboxamine 5:

Diethyl 3-benzyloxycyclobutane-1,1-dicarboxylate 4 (20 g. 65 mmol) was stirred with concentrated aqueous ammonia (250 mL) for four days at room temperature (Step 3). The diamide 5 was collected by filtration and washed with water followed by ethyl acetate. The yield was 8.1 g (50%). $^1$H NMR (d6-DMSO) δ 2.2 (m, 2H, CH$_2$), 2.5 (m, 2H, CH$_2$), 3.8 (q, J=7.2 Hz 1H OCH), 4.3 (s, 2H, OCH$_2$), 7.0 (m, 4H, NH$_2$), 7.23 (s, 5H, phenyl).

Synthesis of cis/trans 5-(3-benzyloxycyclobutane)hydantoin 6:

3-Benzyloxycyclobutane-1, 1-dicarboxamine, 5 (2.0 g, 8 mmol) was stirred in 150 mL of dilute sodium hypochlorite (Aldrich product/water 1 to 2) at 0°–5° C. for four hrs (Step 4). The reaction mixture stood overnight at room temperature. Unreacted diamide was recovered by filtration. The solution was neutralized to pH 5 with concentrated hydrochloric acid and evaporated to dryness in vacuo. The residue was extracted with 50 mL of hot methanol, filtered, and washed with 50 mL of hot methanol. The methanol solutions were combined and evaporated. Yield of the mixture of cis and trans hydantoins 6 was 1.4 g(70%).

Synthesis of 1-amino-3-benzyloxycyclobutane-1-carboxylic acid 7:

The hydantoin 6 (1.0 g,4.1 mmol) was hydrolyzed by refluxing with 10 mL of a barium hydroxide solution (saturated at room temperature) for 16 hr (Step 5). The solution was neutralized to pH 6 with 2M sulfuric acid and evaporated to dryness in vacuo. The residue was extracted with 50 mL of hot methanol, filtered, and washed with 50 mL of hot methanol. The methanol solutions were combined and evaporated. Yield of the 1-amino-3-benzyloxycyclobutane-1-carboxylic acid 7 was 0.69 g(76%). $^1$H NMR (d$_4$-methanol) δ 2.2–2.9 (m, 4H, CH$_2$), 4.3 (t, J=6.9 Hz, 1H, OCH), 4.5 (s, 2H, OCH$_2$), 7.23 (br s, 5H, phenyl)

Synthesis of 1-t-butylcarbamate-3-benzyloxycyclobutane-1-carboxylic acid 8:

A solution of the amino acid 7 (0.5 g, 2.3 mmol) in 10 mL of a mixture of methanol/triethylamine (90:10) was treated with 1.0 g (4.6 mmol) of di-tert-butyldicarbonate (Step 6). The mixture was heated at 50°–60° C. for 10 min and then the solvent was removed by rotoevaporation. The crude product was stirred in 5 mL of dilute HCl (pH=2) at 0° C. for 10 min. The mixture was extracted with $CH_2Cl_2$ (2×10 mL), the combined extract dried, and the solvent was removed. The crude oil was chromatographed on silica gel using methylene chloride/methanol (9 to 1) with 0.1% formic acid. The product 8 (0.55 g, 78%) showed a single spot on TLC (Rf=0.59) with the same solvent system; visualization was with $MoO.H_3PO_4$.

Synthesis of 1-t-butylcarbamate-3-benzyloxycyclobutane-1-carboxylic-methyl ester 9:

To a slurry of 1-methyl-3-nitro-1-nitrosoguandine (150 mg) in 8 mL of ether at 0°–5° C. was added a 40% solution of potassium hydroxide dropwise. The resultant diazomethane ether solution was added to 0.15 g(0.50 mmol) of 1-t-butyl carbamate-3-benzyloxycyclobutane-1-carboxylic methyl ester acid in 3 mL of ether (Step 7) and the mixture was stirred at room temperature for 15 min. The mixture was washed with water (10 mL) and the ether evaporated. The crude residue was chromatographed on silica gel using ethyl acetate/hexane (1 to 9). Yield: 0.13 g (82%); $^1H$ NMR ($CDCl_3$) δ 1.35 (s, 9H, $CH_3$), 2.27–2.88 (m, 4H, $CH_2$), 3.72 (s, 3H, $CH_3$) 4.18 (m, 1H, CHO), 4.42 (s, 2H, $OCH_2$), 7.23 (br s, 5H, phenyl).

Synthesis of 1-t-butylcarbamate-3-hydroxy-cyclobutane-1-carboxylic acid methyl ester 10:

A solution of 0.10 g (0.3 mmol) of the protected amino acid benzyl ether 9 in 5 mL of methanol was mixed with a suspension of 25 mg of 10% palladium on charcoal in 5 mL of methanol (Step 8). The mixture was stirred under a positive pressure of hydrogen (balloon) for 16 hr. The catalyst was filtered off and the solvent was evaporated. The crude residue was chromatographed on silica gel using methylene chloride/methanol (9 to 1). The product 10 (74 mg 89%) showed a single spot on TLC (Rf=0.81) with the same solvent system; visualization was with $MoO.H_3PO_4$.

Synthesis of 1-t-butylcarbamate-3-trifluoromethane sulfonoxy-cyclobutane-1-carboxylic acid methyl ester 11:

The alcohol 10 (25 mg, 0.10 mmol) was dissolved in 10 mL of dry methylene chloride and pyridine (12 μL) by stirring under $N_2$. The solution was cooled to 0°–5° C. and 12 μL of trifluoromethane sulfonic anhydride was added (Step 9). After 1 hr, the solvent was removed in vacuo and the crude oil was chromatographed on silica gel using ethyl acetate/hexane (3 to 7). The product 11 (24 mg, 64%) showed a single spot on TLC (Rf=0.60) with the same solvent system; visualization was with $MoO.H_3PO_4$.

Synthesis of 3-[$^{18}F$]-fluoro-cyclobutane-1-amino-1-carboxylic acid [$^{18}F$] FACBC 13:

[$^{18}F$]-Fluoride was produced using the $^{18}O(p,n)^{18}F$ reaction with 11 MeV protons on 95% enriched [$^{18}O$] water. After evaporation of the water and drying of the fluoride by acetonitrile evaporation, the protected amino acid triflate 11 (3 mg) was introduced in an acetonitrile solution (1 mL). The no carrier added (NCA) fluorination reaction (Step 10) was performed at 85° C. for 5 min in a sealed vessel in the presence of potassium carbonate and Kryptofix (Trademark Aldrich Chemical Co., Milwaukee, Wis.). Unreacted $^{18}F$- was removed by diluting the reacting mixture with methylene chloride followed by passage through a silica gel Seppak which gave the $^{18}F$ labeled product 12 in 42% E.O.B. yield.

Deprotection of 12 (Step 11) was achieved by using 1 mL of 4N HCl at 115° C. for 15 min and then the aqueous solution containing $^{18}FACBC$ 13 was passed through an ion-retardation resin (AG 11A8 50–100 mesh). The synthesis was completed in 60 min following E.O.B. with an overall radiochemical yield of 12% (17.5% E.O.B.).

EXAMPLE 2

Synthesis of [$^{18}F$]-2-Amino-3-fluoro-2-methylpropane-1-carboxylic acid 24 (FAMPC)

3-Benzyloxy-1,2-epoxypropane 15

Sodium hydride (60% oil dispersion, 23.6 g, 0.59 mol) was added in portions to a solution of glycidol (14) (40 g, 0.54 mol), benzyl bromide (101.5 g, 0.59 mol), and n-butylammonium iodide (0.24 g) in dry DMF (150 mL) at 25° C. (Step 12). The mixture was stirred for 1 hr at 65° C., poured over ice and then extracted with ether (2×75 mL). The combined ether extract was washed with water (3×75 mL) and dried over $MgSO_4$. Distillation using a 12-in vigreux column afforded 62.9 g (71%) of glycidyl

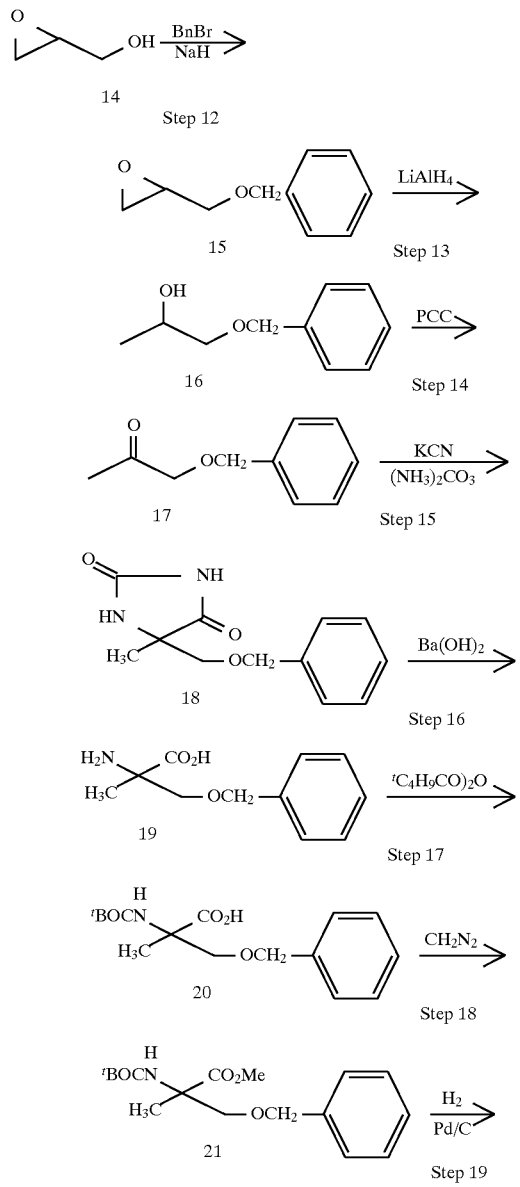

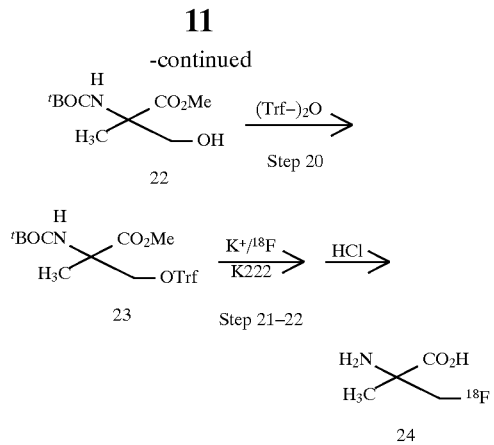

Step 20

Step 21-22 benzyl ether 15; bp 120°–122° C. (10 mm); $^1$H NMR (CDCl$_3$) δ 2.6 (dd, 1H, OCHa), 2.8 (dd, 1H, OCHb), 3.2 (m, 1H, OCHc), 3.2 (dd, 1H, OCHd), 3.8 (dd, 1H, OCHe), 4.6 (dd, 2H, OCH$_2$), 7.23 (s, 5H, phenyl).

3-Benzyloxypropan-2-ol 16

To a suspension of lithium aluminum hydride (6.1 g, 0.16 mol) in ether (50 mL) at 25° C. was added a solution of glycidyl benzyl ether 15 (52.9 g, 0.32 mol) in 50 mL of ether (Step 13). The mixture was refluxed for 2 h and cooled to room temperature. A solution of 1N NaOH was added dropwise to the mixture and the precipitated metal salts were removed by filtration. The ether containing the product was washed with water (50 mL), dried (MgSO$_4$) and the solvent removed by roto-evaporation. Distillation gave 43.3 g (82%) of 3-benzyoxypropan-2-ol; 16 bp 110–112 (5 mm). $^1$H NMR (CDCl$_3$) δ 1.13 (d, J=6.6 Hz, 3H, CH$_3$), 2.5 (br s, 1H, OH), 3.28 (dd, 1H, OCH), 3.45 (dd, 1H, OCH), 4.0 (m, 1H, OCH), 4.55 (s, 2H, OCH$_2$), 7.35 (s, 5H, phenyl).

3-Benzyloxypropan-2-one 17

3-Benzyoxypropan-2-ol 16 (40 g, 0.24 mol) was added to a suspension of pyridinium chlorochromate (155.2 g, 0.72 mol) in DMF (150 ml) at 25° C., stirred at 65° C. for 3 h, and then diluted with water (75 mL) (Step 14). The mixture was extracted with ether (2×50 mL) and the combined ether layers were washed with water (3×50 mL) dried (MgSO$_4$) and the solvent removed by roto-evaporation. Distillation gave 31 g (77%) of 3-benzyloxypropan-2-one; 17 bp 104–106 (10 mm). $^1$H NMR (CDCl$_3$) δ 2.16 (s, 3H, CH$_3$), 4.05 (s, 1H, OH), 4.59 (s, 2H, OCH$_2$), 7.5 (s, 5H, phenyl).

2-(3-benzyloxypropane)hydantoin 18

3-Benzyloxypropan-2-one 17 (25 g, 0.15 mol) was dissolved in 300 mL of 50% ethanol containing ammonium carbonate (68.3 g, 0.60 mol) and potassium cyanide (19.5 g, 0.30 mol) was added. The mixture was warmed to 60° C. for 2 h and evaporated to dryness in vacuo (Step 15). The residue was extracted with 75 mL of hot methanol, filtered, and filter cake washed with 50 mL of hot methanol. The methanol solutions were combined, solvent evaporated, and the residue chromatographed on silica gel using CH$_2$Cl$_2$/methanol 90:10. Yield of 3-benzyloxypropan-2-one hydantoin 18 was 23 g (66%). $^1$H NMR (d4-methanol) δ 1.22 (s, 3H, CH$_3$), 3.41 (d, J=9.6 Hz, 1H, OCHa), 3.52 (d, J=9.6 Hz 1H, OCHb), 4.5 (s, 2H, NH), 4.8 (s, 2H, OCH$_2$), 8.25 (m, 5H, phenyl).

2-Amino-3-benzyloxy-2-methyl-1-propionic acid 19

The hydantoin 18 (6.0 g, 25.6 mmol) was hydrolyzed by refluxing with 20 mL of a barium hydroxide solution (saturated at room temperature) for 16 hr (Step 16). The solution was neutralized to pH 6 with 2 M sulfuric acid and evaporated to dryness in vacuo. The residue was extracted with 50 mL of hot methanol, filtered, and washed with 50 mL of hot methanol. The methanol solutions were combined and evaporated. Yield of the amino acid 19 was 4.1 g (76%).

2-t-Butyl carbamate-3-benzyloxy-2-methyl-1-propionic acid 20

A solution of the amino acid 19 in 10 mL of a mixture of methanol-triethylamine (90:10) is treated with 1.0 g (4.6 mmol) of di-tert-butyl dicarbonate (Step 17). The mixture is heated at 50°–60° C. for 10 min and then the solvent removed by roto-evaporation. The crude product is stirred in 5 mL of dilute HCl (pH=2) at 0° C. for 10 min. The mixture is extracted with CH$_2$Cl$_2$ (2×10 mL), the combined extract dried, and the solvent removed.

The crude oil, 20, is chromatographed on Silica gel using methylene chloride/methanol (9 to 1) with 0.1% formic acid.

2-(t-Butyl carbamate)-3-benzyloxy-2-methyl-1-methylpropionate 21

To a slurry of 1-methyl-3-nitro-1-nitrosoguandine in ether at 0°–5° C. is added a 40% solution of potassium hydroxide dropwise. The resultant diazomethane ether solution is added to 1-t-butyl carbamate-3-benzyloxy-1-methylpropane-1-carboxylic acid 20 in 3 mL of ether and the mixture is stirred at room temperature for 15 min (Step 18). The mixture is washed with water (20 mL) and the ether evaporated. The crude residue 21 is chromatographed on silica gel using ethyl acetate/hexane (1 to 9).

2-(t-Butyl carbamate)-3-hydroxy-2-methyl-1-propionate 22

A solution of the protected amino acid benzyl ether 21 in 5 mL of methanol is mixed with a suspension of 25 mg of 10% palladium on charcoal in 5 mL of methanol (Step 19). The mixture is stirred under a positive pressure of hydrogen (balloon) for 16 hr. The catalyst is filtered off and the solvent is evaporated. The crude residue is chromatographed on silica gel using methylene chloride (9 to 1) to yield 22.

2-(t-Butyl carbamate)-3-trifluoromethane sulfonoxy-2-methyl-1-methylpropionate 23

The alcohol 22 is dissolved in 10 mL of dry methylene chloride and pyridine (12 μL) by stirring under N$_2$. The solution is cooled to 0°–5° C. and 12 μL of trifluoromethane sulfonic anhydride is added (Step 20). After 1 hr, the solvent is removed in vacuo and the crude oil is chromatographed on silica gel using ethyl acetate/hexane (3:7) to yield 23.

[$^{18}$F]-2-Amino-3-fluoro-2-methyl-1-propionic acid 24

[$^{18}$F]-Fluoride is produced using the $^{18}$O(p,n) $^{18}$F reaction with 11 MeV protons on 95% enriched [$^{18}$O] water. After evaporation of the water and drying of the fluoride by acetonitrile evaporation, the protected amino acid triflate 23 (3 mg) is introduced in a acetonitrile solution (1 mL). The (NCA) fluorination reaction (Step 21) is performed at 85° C. for 5 min in a sealed vessel in the presence of potassium carbonate and Kryptofix. Unreacted $^{18}$F$^-$ is removed by diluting the reacting mixture with methylene chloride followed by passage through a silica gel Seppak which gives the $^{18}$F labeled product. Deprotection (Step 22) is achieved by using 1 mL of 4N HCl at 115° C. for 15 min and then the aqueous solution is passed through an ion-retardation resin (AG 11A8 50–100 mesh) to yield 24.

EXAMPLE 3

Synthesis of [$^{18}$F]-1-Amino-3-fluoro-cyclopentane-1-carboxylic acid 37 (FACPC)

4-Bromo-1,2-epoxybutane 26

A solution of m-chloroperbenzoic acid (50% pure, 72.5 g, 0.21 mol) in 500 mL of methylene chloride was added dropwise to a stirred ice-cooled solution of 4-bromo-1-butene 25 (25 g, 0.19 mol) in 100 mL of methylene chloride (Step 23). After the addition, the mixture was stirred at 25° C. for 18 h, during which time m-chlorobenzoic acid precipitated. The reaction mixture was washed with 4N sodium hydroxide until the aqueous phase remained alkaline and with water until neutral. The organic phase was dried (MgSO$_4$) and the solvent removed in vacuo to give 27.9 g (89%) of 4-bromo-1,2-epoxybutane 26. $^1$H NMR (CDCl$_3$) δ 2.10 (m, 2H, O—C—CH$_2$), 2.58 (d,d J=5.0, 2.6 Hz, 1H, OCHa) 2.82 (dd J=5.0,4.0 Hz), 1H, OCHb), 3.09 (m, 2H, O—C—CH$_2$, 3.55 (t, J=7 Hz, 2H).

Diethyl 3-hydroxycyclopentane-1,1-dicarbonate 27

A solution of diethyl malonate (7.7 g, 48.5 mmol) in 53.4 mL of 1N ethanolic sodium ethoxide was stirred for 15 min in a ice bath, after which 4-bromo-1,2-epoxybutane 26 (14.6 g, 97 mmol) was added (Step 24). After stirring at 25° C. for 3 h, the mixture was poured into water and the ethanol evaporated in vacuo. The aqueous solution was extracted with chloroform, the extracts dried (MgSO$_4$) and concentrated. Distillation gave 8.14 g (73%) of product 27; bp 155°–160° C. (0.5 mm); $^1$H NMR (CDCl$_3$) δ 1.3 (t, J=7.2 Hz, 6H, CH$_3$), 1.7–2.7 (m, 6H, CH$_2$), 3.02 (s, 1H, OH), 4.2 (q, J=7.2 Hz, 4H, O=COCH$_2$), 4.2 (m, 1H, OCH).

Diethyl 3-benzyloxycyclopentane-1,1-dicarboxylate 28

Sodium hydride (60% oil dispersion, 2.1 g, 53 mmol) was added in portions to a solution of diethyl 3-hydroxycyclopentane-1,1-dicarboxylate 27 (11 g, 48 mmol), benzyl bromide (9.7 g, 53 mol), and n-tetrabutylammonium iodide (100 mg) in dry DMF (50 mL) at 25° C. (Step 25). The mixture was stirred for 1 hr at 65° C., poured onto ice and then extracted with ether (2×50 mL). The

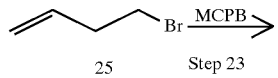
25    Step 23

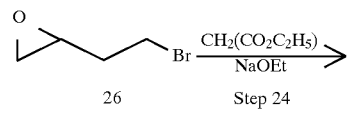
26    Step 24

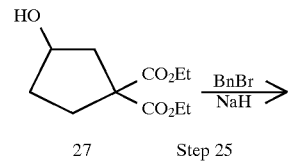
27    Step 25

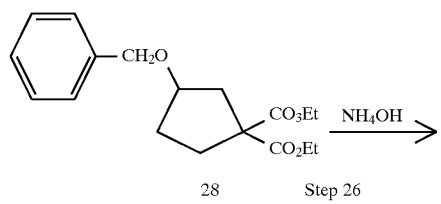
28    Step 26

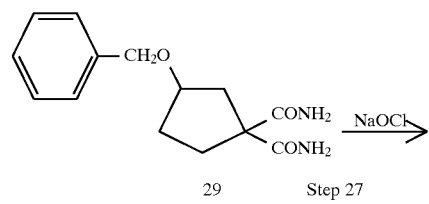
29    Step 27

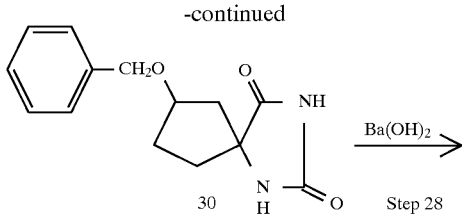
30    Step 28

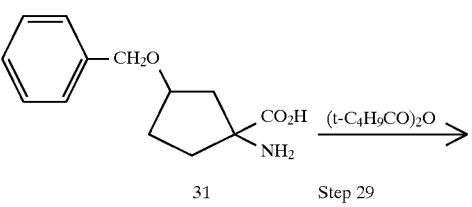
31    Step 29

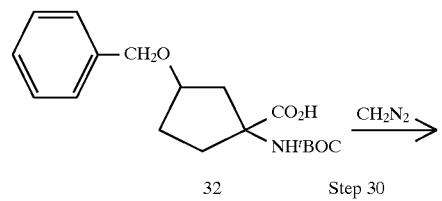
32    Step 30

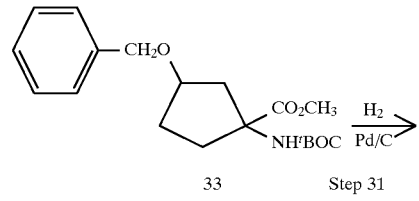
33    Step 31

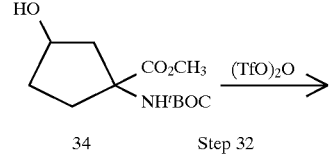
34    Step 32

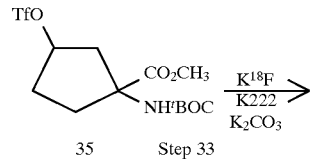
35    Step 33

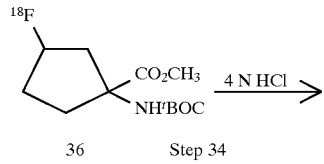
36    Step 34

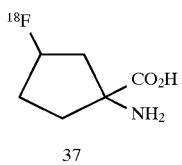
37 combined either extract was washed with water (3×50 mL) and driedover MgSO$_4$. Chromatography on silica gel (10:90 ethyl acetate/hexane, Rf=0.38) afforded 11.6 g (75%) of the benzyl ether 28; $^1$H NMR (CDCl$_3$) δ 1.3 (t, J=7.2 Hz, 6H, CH$_3$), 1.7–2.7 (m, 6H, CH$_2$), 4.2 (q, J=7.2 Hz, 4H, O=COCH$_2$), 4.1 (m, 1H, O—CH), 4.6 (s, 2H, O—CH$_2$), 7.3 (s, 5H, phenyl).

3-Benzyloxycyclopentane-1,1-dicarboxamine 29

Diethyl 3-benzyloxycyclopentane-1,1-dicarboxylate 28 (10 g, 31 mmol) is stirred with concentrated aqueous ammonia (100 mL) for four days at room temperature (Step 26). The resultant diamide 29 is collected by filtration and washed with water followed by ethyl acetate.

Cis/trans 5-(3-benzyloxycyclopentane)hydantoin 30

3-Benzyloxycyclopentane-1,1-dicarboxamine 29 is stirred in 150 mL of dilute sodium hypochlorite (Aldrich product/water 1:2) at 0°–5° C. for 4 hr and then allowed to stand overnight at room temperature (Step 26). Unreacted diamide will be recovered by filtration. The solution is neutralized to pH 5 with concentrated hydrochloric acid and evaporated to dryness in vacuo. The residue is extracted with 50 mL of hot methanol, filtered, and washed with 50 mL of hot methanol. The methanol solutions are combined and evaporated.

1-Amino-3-benzyloxycylcopentanecarboxylate acid 31

The hydantoin 30 is hydrolyzed by refluxing with 10 mL of a barium hydroxide solution (saturated at room temperature) for 16 hr (Step 28). The solution is neutralized to pH 6 with 2 M sulfuric acid and evaporated to dryness in vacuo. The residue is extracted with 50 mL of hot methanol, filtered, and washed with 50 mL of hot methanol. The methanol solutions are combined and evaporated.

1-t-Butyl carbamate-3-benzyloxy-1-cyclopentane-1-carboxylic acid 32

A solution of the amino acid 31 in 10 mL of a mixture of methanol/triethylamine (90:10) is treated with di-tert-butyl dicarbonate (Step 29). The mixture is heated at 50–60° C. for 10 min and then the solvent is removed by rotoevaporation. The crude product is stirred in 5 mL of dilute HCl (pH=2) at 0° C. for 10 min. The mixture is extracted with $CH_2Cl_2$ (2×10 mL), the combined extract dried, and the solvent removed. The crude oil is chromatographed on silica gel using methylene chloride/methanol (9 to 1) with 0.1% formic acid to yield 32.

1-t-Butyl carbamate-3-benzyloxy-1-cyclopentane-1-carboxylic acid methyl ester 33

To a slurry of 1-methyl-3-nitro-1-nitrosoguandine in ether at 0°–5° C. will be added to a 40% solution of potassium hydroxide dropwise. The resultant diazomethane ether solution is added to 1-t-butyl carbamate-3-benzyloxycyclopentane-1-carboxylic acid 32 in 3 mL of ether and the mixture is stirred at room temperature for 15 min (Step 30). The mixture is washed with water (10 mL) and the ether evaporated. The crude residue is chromatographed on silica gel using ethyl acetate/hexane (1 to 9) to yield 33.

1-t-Butyl carbamate-3-hydroxy-1-cyclopentane-1-carboxylic acid methyl ester 34

A solution of the protected amino acid benzyl ether 33 in 5 mL of methanol is mixed with a suspension of 25 mg of 10% palladium on charcoal in 5 mL of methanol (Step 31). The mixture is stirred under a positive pressure of hydrogen (balloon) for 16 hr. The catalyst is filtered off and the solvent is evaporated. The crude residue is chromatographed on silica gel using methylene chloride/methanol (9 to 1) to yield 34.

1-t-Butyl carbamate-3-trifluoromethane sulfonoxy-1-cyclopentane-1-carboxylic carboxylic acid methyl ester 35

The alcohol is dissolved in 10 mL of dry methylene chloride and pyridine (12 μL) by stirring under $N_2$. The solution is cooled to 0°–5° C. and 12 μL of trifluoromethane sulfonic anhydride is added (Step 32). After 1 hr, the solvent is removed in vacuo and the crude oil is chromatographed on silica gel using ethyl acetate/hexane (3:7) to yield 35.

[$^{18}$F]-1-Amino-3-fluorocyclopentane-1-carboxylic acid 37

[$^{18}$F]-Fluoride will be produced using the $^{18}$O(p,n)$^{18}$F reaction with 11 MeV protons on 95% enriched [$^{18}$O] water. After evaporation of the water and drying of the fluoride by acetonitrile evaporation, the protected amino acid triflate 35 (3 mg) is introduced in an acetonitrile solution (1 mL). The (NCA) fluorination reaction is performed at 85° C. for 5 min in a sealed vessel in the presence of potassium carbonate and Kryptofix (Step 33). Unreacted $^{18}$F$^-$ is removed by diluting the reacting mixture with methylene chloride followed by passage through a silica gel Seppak which gives the $^{18}$F labeled product 36. Deprotection (Step 34) is achieved by using 1 mL of 4N HCl at 115° C. for 15 min and then the aqueous solution is passed through an ion-retardation resin (AG 11A8 50–100 mesh) to yield 37 (FACPC).

EXAMPLE 4

[$^{18}$F]-1-Amino-4-fluoro-cyclohexane-1-carboxylic acid 49 (FACHC)

4-Hydroxycyclohexanone ethylene ketal 49

Sodium borohydrate (2.4 g, 64 mmol) was added in portions to a stirred ice cold solution of 1,4 cyclohexanedione monoethylene ketal 38 (20 g, 128 mmol) in 60 mL of methanol (Step 35). After addition was complete, 1N HCl was added to the solution dropwise until a pH of 8 was obtained and then the solvent was removed by rotoevaporation. The product 39 (16.8 g, 84%) showed a single spot on TLC (Rf=0.4, ethyl acetate/hexane 20:80 solvent system, visualization was with acidic vanillin ethanol solution) and was used without further purification. $^1$H NMR (CDCl$_3$) δ 1.6–1.9 (m, 8H, ring-CH$_2$), 3.8 (m, 1H, CH-O), 4.0 (s, 4H, ketal-CH$_2$), 5.3 (s, 1H, OH).

4-Benzyloxycyclohexanone ethylene ketal 40

Sodium hydride (60% oil dispersion, 2.2 g, 56 mmol) was added in portions to a solution of 6-hydroxycyclohexanone ethylene ketal (39) (8.8 g, 51 mmol), benzyl bromide (9.6 g, 5.6 mmol), and tetra-n-butylammonium iodide (50 mg) in dry DMF (50 mL) at 25° C. (Step 36). The mixture was stirred for 1 hr at 65° C., poured over ice and then extracted with ether (2×50 mL). The combined ether extract was

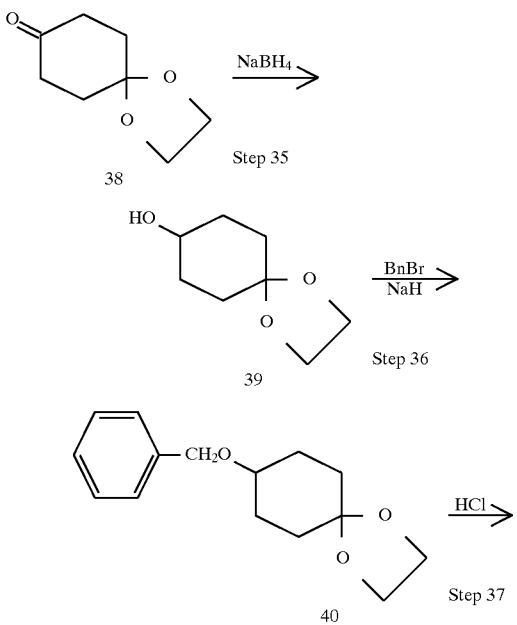

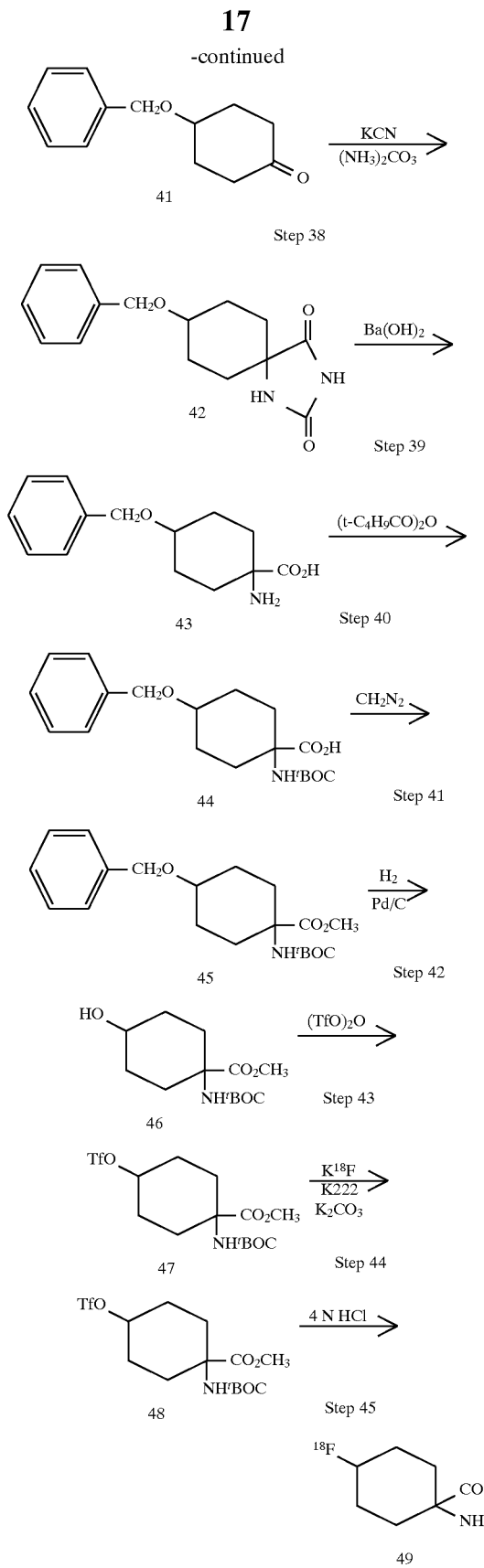

washed with water (3×50 mL), dried (MgSO$_4$) and solvent was removed. Chromatography on silica gel using 10:90 ethyl acetate/hexane (Rf=0.39) afforded 8.9 g (70%) of the benzyl ether 40. $^1$H NMR (CDCl$_3$) δ 1.6–1.9 (m, 8H, ring-CH$_2$), 3.6 (m, 1H, CH—O), 4.0 (2, 4H, ketal—CH$_2$), 4.6 (s, 2H, CH$_2$—O).

4-Benzyloxycyclohexanone 41

A solution of 4-benzyloxy cyclohexanone ethylene ketal 40 (5.0 g, 20.1 mmol) in methanol (20 mL) and 1N HCl (0.5 mL) was stirred overnight at 25° C. (Step 37). The mixture was neutralized by addition of 1N NaHCO$_3$ (0.5 mL), solvent removed by roto-evaporation, and the residue chromatographed on silica gel using 15:85 ethyl acetate/hexane. Yield of the ketone 41 was 2.7 g (67%); Rf=0.35; $^1$H NMR (CDCl$_3$) δ 2.3 (m, 8H, ring—CH$_2$) 3.6 (m, 1H, CH—O), 4.6 (s, 2H, CH$_2$—O).

4-Benzyloxycyclohexanone hydantoin 42

4-Benzyloxycyclohexanone 41 is dissolved in 30 mL of 50% ethanol containing ammonium carbonate and potassium cyanide is added (Step 38). The mixture will be warmed to 60° C. for 2 h and evaporated to dryness in vacuo. The residue is extracted with 40 mL of hot methanol, filtered, and the filter cake washed with 20 mL of hot methanol. The methanol solutions are combined, solvent evaporated, and the residue chromatographed on silica gel using CH$_2$Cl$_2$/methanol 90:10 to yield 42.

1-Amino-4-benzyloxycyclohexane-1-carboxylic acid 43

The hydantoin 42 is hydrolyzed by refluxing with 10 mL of a barium hydroxide solution (saturated at room temperature) for 16 h (Step 39). The solution is neutralized to pH 6 with 2N sulfuric acid and evaporated to dryness in vacuo. The residue is extracted with 50 mL of hot methanol, filtered, and washed with 50 mL of hot methanol. The methanol solutions are combined and evaporated.

1-t-Butyl carbamate-3-benzyloxy-1-cyclohexane-1-carboxylic acid 44

A solution of the amino acid in 10 mL of a mixture of methanol/triethylamine (90:10) is treated with di-tert-butyl dicarbonate (Step 40). The mixture is heated at 50°–60° C. for 10 min and then the solvent is removed by rotoevaporation. The crude product is stirred in 5 mL of dilute Hcl (pH=2) at 0° C. for 10 min. The mixture is extracted with CH$_2$Cl$_2$ (2×10 mL), the combined extract dried, and the solvent removed. The crude oil is chromatographed on silica gel using methylene chloride/methanol (9 to 1) with 0.1% formic acid to yield 44.

1-t-Butyl carbamate-3-benzyloxy-1-cyclohexane-1-carboxylic acid methyl ester 45

To a slurry of 1-methyl-3-nitro-1-nitrosoguandine in ether at 0°–5° C. is added to a 40% solution of potassium hydroxide dropwise. The resultant diazomethane ether solution is added to 1-t-Butyl carbamate-3-benzyloxy-1-cyclohexane-1-carboxylic acid 44 in 3 mL of ether and the mixture is stirred at room temperature for 15 min (Step 41). The mixture is washed with water (10 mL) and the ether evaporated. The crude residue is chromatographed on silica gel using ethyl acetate/hexane (1 to 9) to yield 45.

1-t-Butyl carbamate-3-hydroxy-1-cyclobutane-1-carboxylic acid methyl ester 46

A solution of the protected amino acid benzyl ether 45 in 5 mL of methanol is mixed with a suspension of 25 mg of 10% palladium on charcoal in 5 mL of methanol (Step 42). The mixture is stirred under a positive pressure of hydrogen (balloon) for 16 hr. The catalyst is filtered off and the solvent is evaporated. The crude residue is chromatographed on silica gel using methylene chloride/methanol (9 to 1) to yield 46.

1-t-Butyl carbamate-3-trifluoromethane sulfonoxy-1-cyclohexane-1-carboxylic acid methyl ester 47

The alcohol 46 is dissolved in 10 mL of dry methylene chloride and pyridine (12 μL) by stirring under N$_2$. The solution is cooled to 0°–5° C. and 12 μL of trifluoromethane sulfonic anhydride is added (Step 43). After 1 hr, the solvent is removed in vacuo and the crude oil is chromatographed on silica gel using ethyl acetate/hexane (3:7).

[$^{18}$F]-1-Amino-3-fluorocyclohexane-1-carboxylic acid 49

[$^{18}$F]-Fluoride is produced using the $^{18}$O(p,n) $^{18}$F reaction with 11 MeV protons on 95% enriched [$^{18}$O] water. After evaporation of the water and drying of the fluoride by acetonitrile evaporation, the protected amino acid triflate 47 (3 mg) is introduced in an acetonitrile solution (1 mL). The (NCA) fluorination reaction is performed at 85° C. for 5 min in a sealed vessel in the presence of potassium carbonate and Kryptofix (Step 44). Unreacted $^{18}$F$^-$ is removed by diluting the reacting mixture with methylene chloride followed by passage through a silica gel Seppak which gives the $^{18}$F labeled product. Deprotection (Step 45) is achieved by using 1 mL of 4N HCl at 115° C. for 15 min and then the aqueous solution is passed through an ion-retardation resin (AG 11A8 50–100 mesh) to yield FACHC 49.

EXAMPLE 5

[$^{18}$F]-1-Amino-3-(fluoromethyl)cyclobutane-1-carboxylic acid 60

Dimethyl ester 3-hydroxycyclobutane-1,1-dicarboxylate 51

To a slurry of 1-methyl-3-nitro-1-nitrosoguandine (150 mg) in 8 mL of ether at 0°–5° C. was added a 40% solution of potassium hydroxide dropwise. The resultant diazomethane ether solution was added to 0.15 g (0.50 mmol) of 50 in 3 mL of ether and the mixture was stirred at room temperature for 15 min (Step 46). The mixture was washed with water (10 mL) and the ether evaporated. The crude residue was chromatographed on Silica gel.

Dimethyl 3-(benzyloxymethyl)cyclobutane-1,1-dicarboxylate 52

Sodium hydride (60% oil dispersion, 2.1 g, 53 mmol) is added in portions to a solution of dimethyl 3-(hydroxymethyl)cyclobutane-1,1-dicarboxylate (51), benzyl bromide, and n-tetrabutylammonium iodide in dry DMF at 25° C. (Step 47). The mixture is stirred for 1 hr at 65° C., poured onto ice and then extracted with ether (2×50 mL). The combined ether extract is washed with water (3×50 mL) and dried over MgSO$_4$. Chromatography on silica gel.

[18F]-1-Amino-3-(fluoromethyl)cyclobutane-1-carboxylic acid

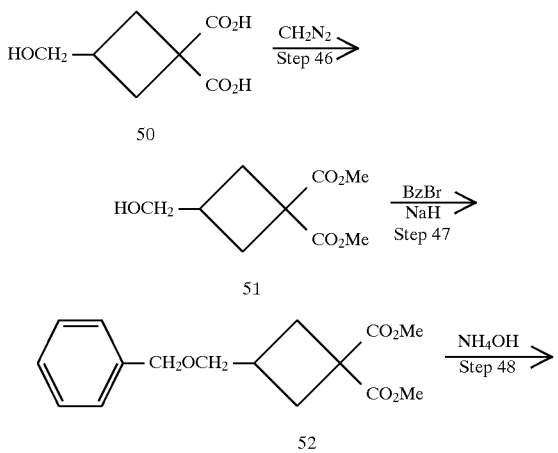

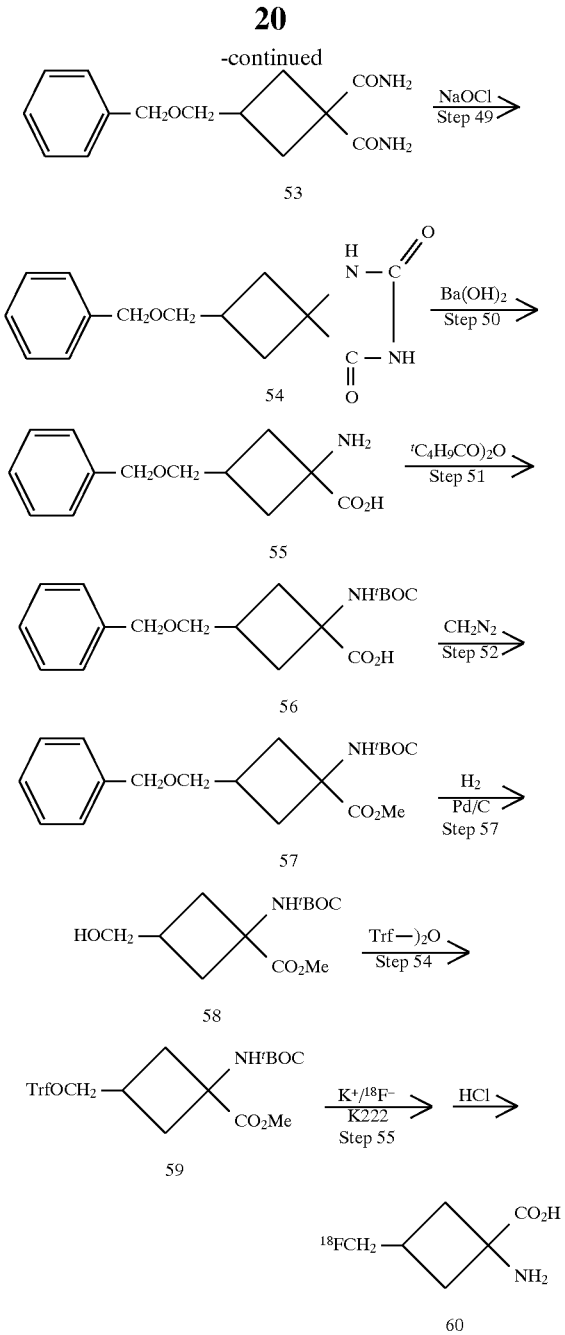

3-(Benzyloxymethyl)cyclobutane-1,1-dicarboxamine 53

Dimethyl 3-(benzyloxymethyl)cyclobutane-1,1-dicarboxylate (52) is stirred with concentrated aqueous ammonia (100 mL) for four days at room temperature (Step 48). The resultant diamide is collected by filtration and washed with water followed by ethyl acetate.

Cis/trans 5-((3-benzyloxymethyl)cyclobutane)hydantoin 54

3-(Benzyloxymethyl)cyclopentane-1,1-dicarboxamine (53) is stirred with dilute sodium hypochlorite (Aldrich product/water 1:2) at 0°–5° C. for 4 hr and then allowed to stand overnight at room temperature (Step 49). Unreacted diamide is recovered by filtration. The solution is neutralized to pH 5 with concentrated hydrochloric acid and evaporated to dryness in vacuo. The residue is extracted with 50 mL of hot methanol, filtered, and washed with 50 mL of hot methanol. The methanol solutions are combined and evaporated.

1-Amino-3-(benzyloxymethyl)cyclobutane-1-carboxylic acid 55

The hydantoin 54 is hydrolyzed by refluxing with 10 mL of a barium hydroxide solution (saturated at room temperature) for 16 hr (Step 50). The solution is neutralized to pH 6 with 2M sulfuric acid and evaporated to dryness in vacuo. The residue is extracted with 50 mL of hot methanol, filtered, and washed with 50 mL of hot methanol. The methanol solutions are combined and evaporated.

1-t-Butyl carbamate-3-(benzyloxymethyl)cyclobutane-1-carboxylicacid

A solution of the amino acid (55) in 10 mL of a mixture of methanol/triethylamine (90:10) is treated with di-tert-butyl dicarbonate (Step 51). The mixture is heated at 50°–60° C. for 10 min and then the solvent is removed by rotoevaporation. The crude product is stirred in 5 mL of dilute HCl (pH=2) at 0° C. for 10 min. The mixture is extracted with $CH_2Cl_2$ (2×10 mL), the combined extract dried, and the solvent removed. The crude oil is chromatographed on silica gel using methylene chloride/methanol (9 to 1) with 0.1% formic acid.

1-t-Butyl carbamate-3-(benzyloxymethyl)cyclobutane-1-carboxylicacid methyl ester 57

To a slurry of 1-methyl-3-nitro-1-nitrosoguandine in ether at 0°–5° C. is added a 40% solution of potassium hydroxide dropwise. The resultant diazomethane ether solution is added to carboxylic acid 56 in ether and the mixture is stirred at room temperature for 15 min. (Step 52). The mixture is washed with water and the ether evaporated. The crude residue is chromatographed on silica gel using ethyl acetate/hexane (1 to 9).

1-t-Butyl carbamate-3-(hydroxymethyl)cyclobutane-1-carboxylic acid methyl ester 58

A solution of the protected amino acid benzyl ether 57 in methanol is mixed with a suspension of 10% palladium on charcoal in 5 mL of methanol (Step 53). The mixture is stirred under a positive pressure of hydrogen (balloon) for 16 hr. The catalyst is filtered off and the solvent is evaporated. The crude residue is chromatographed on silica gel using methylene chloride/methanol (9 to 1).

1-t-Butyl carbamate-3-(trifluoromethane sulfonoxymethyl)cyclobutane-1-carboxylic acid methyl ester 59

The alcohol 58 is dissolved in 10 mL of dry methylene chloride and pyridine (12 µL) by stirring under $N_2$. The solution is cooled to 0°–5° C., and 12 µL of trifluoromethane sulfonic anhydride is added (Step 54). After 1 hr, the solvent is removed in vacuo and the crude oil is chromatographed on silica gel using ethyl acetate/hexane (3:7).

[$^{18}$F]-1-Amino-3-(fluoromethyl)cyclobutane-1-carboxylic acid 60

[$^{18}$F]-Fluoride is produced using the $^{18}O(p,n)^{18}F$ reaction with 11 MeV protons on 95% enriched [$^{18}O$] water. After evaporation of the water and drying of the fluoride by acetonitrile evaporation, the protected amino acid triflate 58 (3 mg) is introduced in an acetonitrile solution (1 mL). The (NCA) fluorination reaction is performed at 85° C. for 5 min in a sealed vessel in the presence of potassium carbonate and Kryptofix (Step 55). Unreacted $^{18}F^-$ is removed by diluting the reacting mixture with methylene chloride followed by passage through a silica gel Seppak which gives the $^{18}F$ labeled product. Deprotection of 59 is achieved by using 1 mL of 4N HCl at 115° C. for 15 min (Step 56) and then aqueous solution is passed through an ion-retardation resin (AG 11A8 50–100 mesh).

EXAMPLE 6

Synthesis of [$^{123}$I]-1-Amino-3-iodocyclobutane-1-carboxylic acid 61

[$^{123}$I]-Sodium iodide (10 mCi, 0.1N NaOH solution) is dried by acetonitrile (2 mL) evaporation, the protected amino acid triflate 11 (3 mg) is introduced in an acetonitrile solution (1 mL) (Step 57). The (NCA) iodination reaction is performed at 85° C. for 5 min in a sealed vessel. Unreacted $^{18}F^-$ is removed by diluting the reacting mixture with methylene chloride followed by passage through a silica gel Seppak which gives the $^{18}I$ labeled product. Deprotection is achieved by using 1 mL of 4N HCl at 115° C. for 15 min (Step 58) and then the aqueous solution is passed through an ion-retardation resin (AG 11A8 50–100 mesh).

EXAMPLE 7

Synthesis of [$^{123}$I]-1-Amino-3-iodocyclobut-2-ene-1-carboxylic acid 65

1-t-Butyl carbamate-3-oxo-1-cyclobutane-1-carboxylic acid methyl ester 62

The protected alcohol 10 is added to a suspension of pyridinium chlorochromate in DMF at 25° C., stirred at 65° C. for 3 h, and then diluted with water (75 mL) (Step 59). The mixture is extracted with ether (2×50 mL) and the combined ether layers were washed with water, dried (MgSO4) and the solvent removed by roto-evaporation.

[1-t-Butyl carbamate-1-cyclobutane-1-carboxylic acid methyl ester] 3-hydrazone 63

A mixture of hydrazine, ketone 62, DBN, and 20 mL of ethanol is heated to boiling (Step 60). The mixture is kept hot for 10 min. The solution is cooled, and the hydrazone is collected by filtration.

[$_{123}$I]-1-Amino-3-iodo-cyclobut-2-ene-1-carboxylic acid 65

Aqueous 3% hydrogen peroxide is added to a mixture of sodium [$_{123}$I]iodide, hydrazone 63, and 0.1N HCl in a sealed vial protected by a charcoal vent (Step 61). The reaction is allowed to proceed for

[123I]-1-Amino-3-iodocyclobutane-1-carboxylic acid

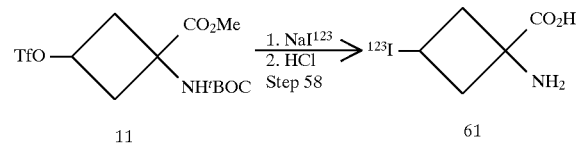

[123I]-1-Amino-3-iodocyclobut-2-ene-1-carboxylic acid

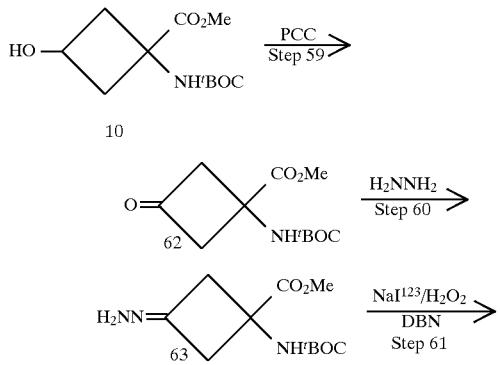

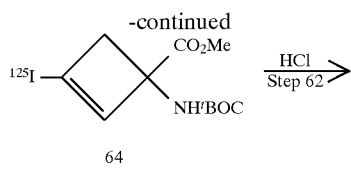

64

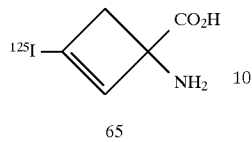

65

30 min at ambient temperature, quenched with a solution of sodium bisulfite (300 mg/mL). Deprotection of 64 (Step 62) is achieved by using 1 mL of 4N HCl at 115° C. for 15 min and then the aqueous solution is passed through an ion-retardation resin (AG 11A8 50–100 mesh).

EXAMPLE 8

Synthesis of E-[$^{123}$I]-1-Amino-3-(2-iodoethenyl)cyclobutane-1-carboxylic acid 69

1-t-Butyl carbamate-3-bromo-1-cyclobutane-1-carboxylic acid methyl ester 66

Bromine is added to a mixture of alcohol 10 and triphenylphosphine in DMF at −10° C. (Step 63). After stirring for 1 h, the mixture is diluted with water and extracted with ether. The ether layer is washed with water, 10% sodium sulfite, and then dried. The ether is removed and the residue is chromatographed on silica gel.

1-t-Butyl carbamate-3-ethynyl-1-cyclobutane-1-carboxylic acid methyl ester 67

The bromo compound 66 in THF is added to a suspension of lithium acetylide ethylenediamine complex in THF stirred at 0° C. under a nitrogen atmosphere (Step 64). The mixture is stirred for 3 h at 25° C., poured into ice water, and extracted with ether. The ether extract is washed with ice cold 1N HCl, brine and then dried. The ether is removed and the residue is chromatographed on silica gel.

1-t-Butyl carbamate-3-((E)-2-tributylstannylethenyl)-1-cyclobutane-1-carboxylic acid methyl ester 68

Tributyltin hydride, the alkyne 67 and azobisisobutyronitrile are refluxed in toluene under nitrogen atmosphere for 10 h (Step 65). The reaction mixture is cooled, solvent removed in vacuo, and the residue chromatographed on silica gel.

[$^{123}$I]-1-Amino-3-((E)-2-iodoethenyl)cyclobut-2-ene-1-carboxylic acid 69

Aqueous 3% hydrogen peroxide is added to a mixture of sodium [$^{125}$I]iodide, tributylstannyl 68, and 0.1N HCl in a sealed vial protected by a charcoal vent (Step 66). The reaction is allowed to

[123I]-1-Amino-3-(2-iodoethenyl)cyclobutane-1-carboxylic acid

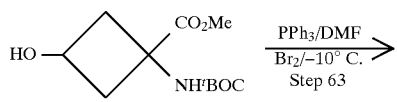

10

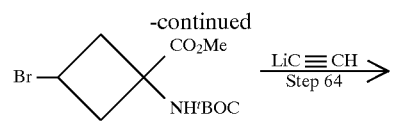

66

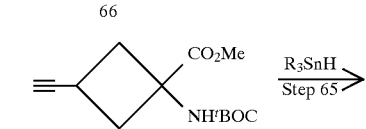

67

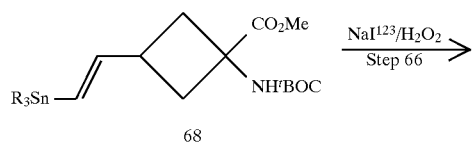

68

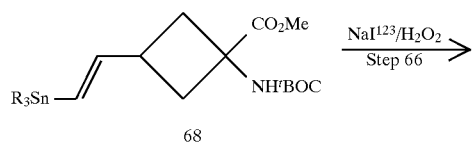

69

[123I]-1-Amino-3-(iodomethylenyl)cyclobutane-1-carboxylic acid

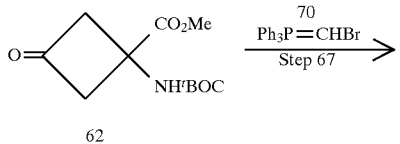

62

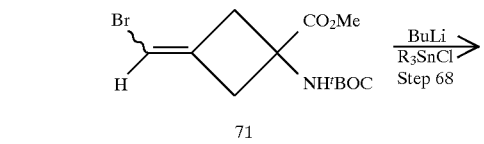

71

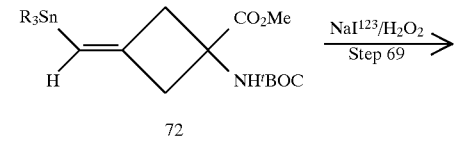

72

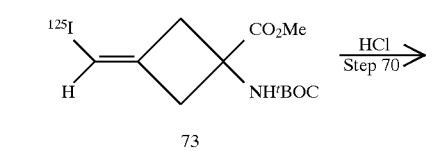

73

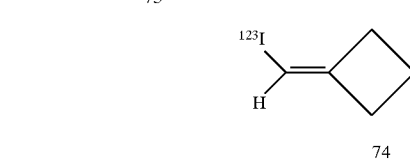

74 proceed for 30 min at ambient temperature, quenched with a solution of sodium bisulfite (300 mg/mL). Deprotection (Step 67) is achieved by using 1 mL of 4N HCl at 115° C. for 15 min and then the aqueous solution is passed through an ion-retardation resin (AG 11A8 50–100 mesh).

EXAMPLE 9
Synthesis of [$^{123}$I]-1-Amino-3-(iodomethylenyl) cyclobutane-1-carboxylic acid
(Bromomethyl)triphenylphosphonium bromide 70

A mixture of hydroxymethyl)triphenylphosphonium bromide and phosphorus tribromide in benzene is heated at reflux for 23 h with stirring. After this time the solution is dark orange and an orange solid is present The mixture is cooled to 25° C. and methanol is added. The solvent was removed at reduced pressure and the residue treated with water to extract the phosphonium salt. The aqueous extracts were saturated with solid potassium bromide and extracted with chloroform. The phosphonium salts are crystallized from hot chloroform by addition of ethyl acetate.
1-t-Butyl carbamate-3-(bromomethylenyl)-1-cyclobutane-1-carboxylic acid methyl ester 71

The phosphonium salt 70 is suspended in ether and ethereal phenyllithium is added rapidly at 25° C. An orange-yellow solution results which becomes mustard yellow within 2 h. To this solution is added protected ketone 62 and the reaction mixture is heated at reflux for 8 h with stirring (Step 68). The ether is removed and the residue is chromatographed on silica gel.
1-t-Butyl carbamate-3-(tributylstannylmethylenyl)-1-cyclobutane-1-carboxylic acid methyl ester 72

To a solution of 71 in ether at −78° C. is added t-butyllithium (2 eq.) after 15 min tributyltin chloride is added and the mixture is warmed to 25° C. (Step 69). The reaction mixture is poured into ice water and the ether layer separated and dried. The ether is removed and the residue is chromatographed on silica gel.
[$^{123}$I]-1-Amino-3-(iodomethylenyl)cyclobutane-1-carboxylic acid 74

Aqueous 3% hydrogen peroxide is added to a mixture of sodium [$^{125}$I]iodide, tributylstannyl 72, and 0.1N HCl in a sealed vial protected by a charcoal vent (Step 70). The reaction is allowed to proceed for 30 min at ambient temperature, quenched with a solution of sodium bisulfite (300 mg/mL). Deprotection of 73 (Step 71) is achieved by using 1 mL of 4N HCl at 115° C. for 15 min and then the aqueous solution is passed through an ion-retardation resin (AG 11A8 50–100 mesh).

EXAMPLE 10
[$^{123}$I]-2-Amino-2-methyl-4-(E)-iodobut-3-en-1-oic acid
2-t-Butyl carbamate-2-methyl-3-carbomethoxy propanol 75

The protected alcohol 22 is added to a suspension of pyridinium chlorochromate in DMF at 25° C., stirred at 65° C. for 3 h, and then diluted with water (75 mL) (Step 72). The mixture is extracted with ether (2×50 mL) and the combined ether layers were washed with water, dried (MgSO$_4$) and the solvent removed by roto-evaporation.
2-t-Butyl carbamate-2-methyl-4-(E)-bromobut-3-en-1-oic acid methyl ester 76

The phosphonium salt 70 is suspended in ether and ethereal phenyllithium is added rapidly at 25° C. An orange-yellow solution results which becomes mustard yellow within 2 h. To this solution is added protected aldehyde 75 and the reaction mixture is heated at reflux for 8 h with stirring (Step 73). The ether is removed and the residue is chromatographed on silica gel.
2-t-Butyl carbamate-2-methyl-4-(E)-tributylstannylbut-3-en-1-oic acid methyl ester 77

To a solution of 76 in ether at −78° C. will be added t-butyllithium (2 eq.) after 15 min tributyltin chloride is added and the mixture is warmed to 25° C. (Step 74). The reaction mixture is poured into ice water and the ether layer separated and dried. The ether is removed and the residue is chromatographed on silica gel.

Synthesis of [123I]-2-Amino -2-methyl-4-(E)-iodobut-3-en-1-oic acid

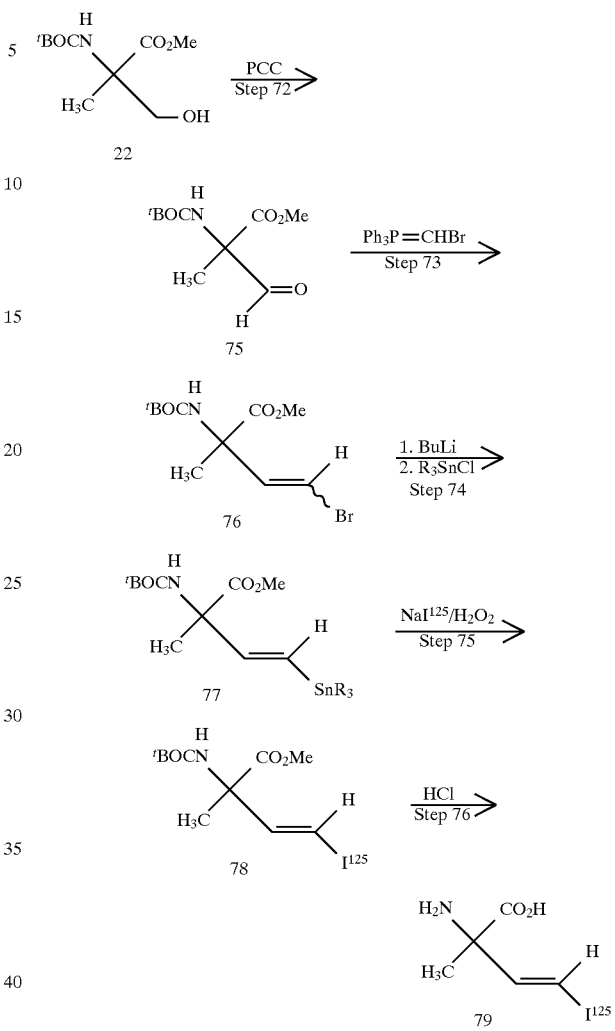

[$^{123}$I]-2-Amino-2-methyl-4-(E)-iodobut-3-en-1-oic acid 79

Aqueous 3% hydrogen peroxide is added to a mixture of sodium [$^{123}$I]iodide, tributylstannyl 77, and 0.1N HCl in a sealed vial protected by a charcoal vent (Step 75). The reaction is allowed to proceed for 30 min at ambient temperature, quenched with a solution of sodium bisulfite (300 mg/mL). Deprotection of 78 (Step 76) is achieved by using 1 mL of 4N HCl at 115° C. for 15 min and then the aqueous solution is passed through an ion-retardation resin (AG 11A8 50–100 mesh).

EXAMPLE 11
Synthesis of [$^{123}$I]-1-Amino-3-iodocyclopentane-1-carboxylic acid 80

[$^{125}$I]-Sodium iodide (10 mCi, 0.1N NaOH solution) is dried by acetonitrile (2 mL) evaporation, the protected amino acid triflate 35 (3 mg) is introduced in an acetonitrile solution (1 mL). The (NCA) iodination reaction is performed at 85° C. for 5 min in a sealed vessel. Unreacted $^{123}$I is removed by diluting the reacting mixture with methylene chloride followed by passage through a silica gel Seppak which gives the $^{123}$I labeled product. Deprotection is achieved by using 1 mL of 4N HCl at 115° C. for 15 min and then the aqueous solution is passed through an ion-retardation resin (AG 11A8 50–100 mesh).

EXAMPLE 12

Synthesis of [$^{123}$I]-1-Amino-3-iodocyclopent-2-ene-1-carboxylic acid 1-t-Butyl carbamate-3-oxo-1-cyclopentane-1-carboxylic acid methyl ester 81

The protected alcohol 34 will be added to a suspension of pyridinium chlorochromate in DMF at 25° C., stirred at 65° C. for 3 h, and then diluted with water (75 mL) (Step 77). The mixture is extracted with ether (2×50 mL) and the combined ether layers are washed with water, dried (MgSO$_4$) and the solvent removed by roto-evaporation.

[123I]-1-Amino-3-iodocyclopentane-1-carboxylic acid X=1

[123I]-1-Amino-4-iodocyclohexane-1-carboxylic acid X=2

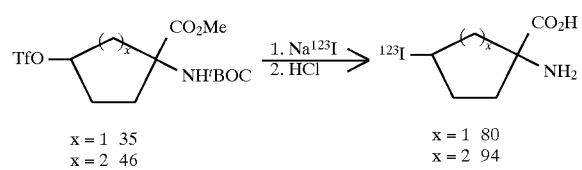

x = 1  35
x = 2  46 x = 1  80
x = 2  94

[123I]-1-Amino-3-iodocyopentane-1-carboxylic acid X=1

[123I]-1-Amino-4-iodocyclohex-2-ene-1-carboxylic acid X=2

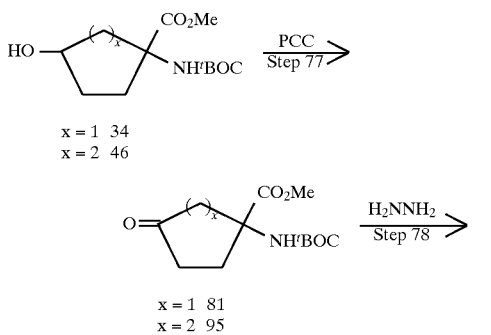

x = 1  34
x = 2  46 x = 1  81
x = 2  95 x = 1  82
x = 2  96

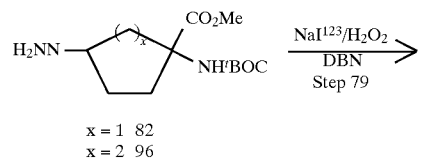

x = 1  83
x = 2  97

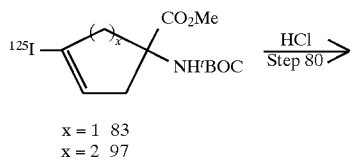

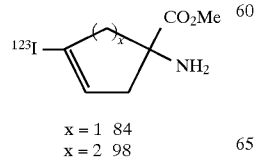

x = 1  84
x = 2  98

[1-t-Butyl carbamate-1-cyclopentane-1-carboxylic acid methyl ester] 3-hydrazone 82

A mixture of hydrazine, the ketone 81, DBN, and 20 mL of ethanol is heated to boiling (Step 78). The mixture is kept hot for 10 min. The solution is cooled, and the hydrazone is collected by filtration.

[$^{123}$I]-1-Amino-3-iodo-cyclopent-2-ene-1-carboxylic acid 84

Aqueous 3% hydrogen peroxide will be added to a mixture of sodium [$^{123}$I]iodide, hydrazone 82, and 0.1N HCl in a sealed vial protected by a charcoal vent (Step 79). The reaction is allowed to proceed for 30 min at ambient temperature, quenched with a solution of sodium bisulfite (300 mg/mL). Deprotection of 83 (Step 80) is achieved by using 1 mL of 4N HCl at 115° C. for 15 min and then the aqueous solution is passed through an ion-retardation resin (AG 11A8 50–100 mesh).

EXAMPLE 13

Synthesis of E-[$^{123}$I]-1-Amino-3-(2-iodoethenyl)cyclopentane-1-carboxylic acid 88

1-t-Butyl carbamate-3-bromo-1-cyclopentane-1-carboxylic acid methyl ester 85

Bromine is added to a mixture of alcohol 34 and triphenylphosphine in DMF at −10° C. (Step 81). After stirring for 1 h, the mixture is diluted with water and extracted with ether. The ether layer is washed with water, 10% sodium sulfite, and then dried. The ether is removed and the residue is chromatographed on silica gel.

1-t-Butyl carbamate-3-ethynyl-1-cyclopentane-1-carboxylic acid methyl ester 86

The bromo compound 85 in THF is added to a suspension of lithium acetylide ethylenediamne complex in THF stirred at 0° C. under a nitrogen atmosphere (Step 82). The mixture is stirred for 3 h at 25° C., poured into ice water, and extracted with ether. The ether extract is washed with ice cold 1N HCl, brine and then dried. The ether is removed and the residue is chromatographed on silica gel.

E-[123I]-1-Amino-4-(2-iodoethenyl)cyclopentane-1-carboxylic acid X=1

E-[123I]-1-Amino-4-(2-iodoethenyl)cyclohexane-1-carboxylic acid X=2

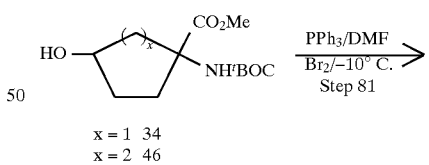

x = 1  34
x = 2  46

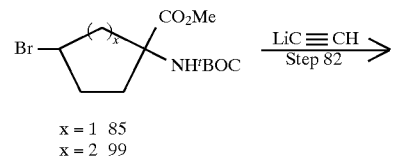

x = 1  85
x = 2  99

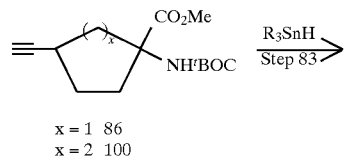

x = 1  86
x = 2  100

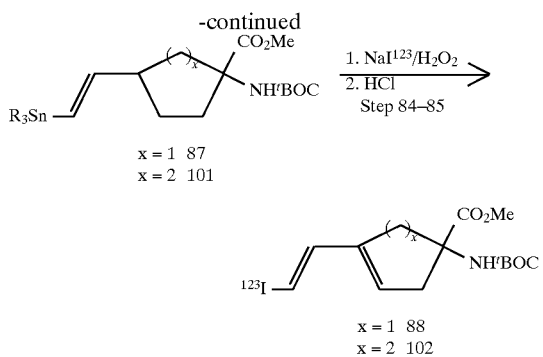

[123I]-Amino-3-(iodomethylenylcyclopentane-1-carboxylic acid X=1

[123I]-1-Amino-4-(iodomethylenyl)cyclohexane-1-carboxylic acid X=2

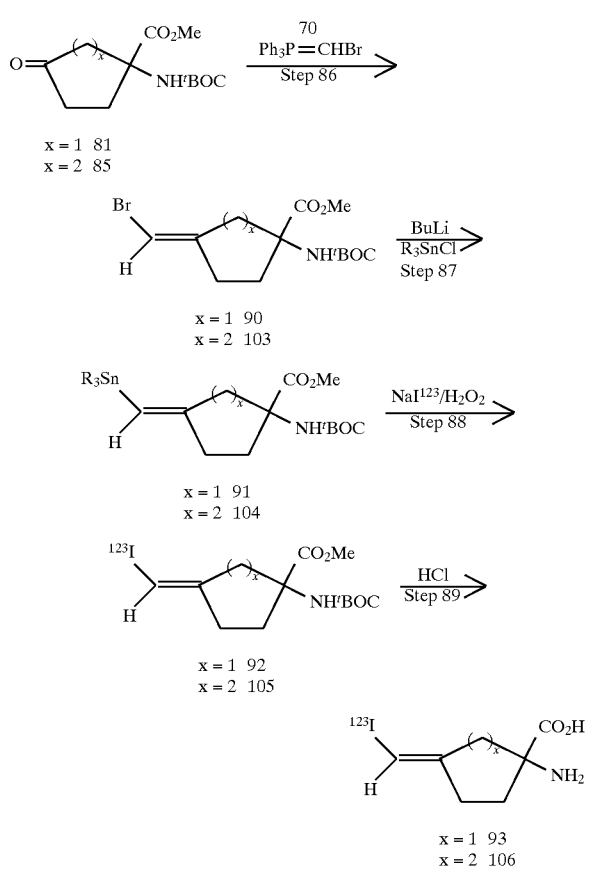

1-t-Butylcarbamate-3-((E)-2-tributylstannylethenyl)-1-cyclopentane-1-carboxylic acid methyl ester 87

Tributyltin hydride, the alkyne 86 and azobisisobutyronitrile will be refluxed in toluene under nitrogen atmosphere for 10 h (Step 83). The reaction mixture is cooled, solvent removed in vacuo, and the residue chromatographed on silica gel.

[$^{123}$I]-1-Amino-3-((E)-2-iodoethenyl)cyclopentane-1-carboxylic acid 88

Aqueous 3% hydrogen peroxide is added to a mixture of sodium [$^{123}$I]iodide, tributylstannyl 87, and 0.1N HCl in a sealed vial protected by a charcoal vent (Step 84). The reaction is allowed to proceed for 30 min at ambient temperature, quenched with a solution of sodium bisulfite (300 mg/mL). Deprotection (Step 85) is achieved by using 1 mL of 4N HCl at 115° C. for 15 min and then the aqueous solution is passed through an ion-retardation resin (AG 11A8 50–100 mesh).

EXAMPLE 14

Synthesis of [$^{123}$I]-1-Amino-3-(iodomethylenyl)cyclopentane-1-carboxylic acid 93

1-t-Butyl carbamate-3-(bromomethylenyl)-1-cyclopentane-1-carboxylic acid methyl ester 90

The phosphonium salt 70 is suspended in ether and ethereal phenyllithium is added rapidly at 25° C. An orange-yellow solution results which becomes mustard yellow within 2 h. To this solution is added protected ketone 81 and the reaction mixture is heated at reflux for 8 h with stirring (Step 86). The ether is removed and the residue is chromatographed on silica gel.

1-t-Butyl carbamate-3-(tributylstannylmethylenyl)-1-cyclopentane-1-carboxylic acid methyl ester 91

To a solution of 90 in ether at −78° C. is added t-butyllithium (2 eq.) after 15 min tributyltin chloride is added and the mixture is warmed to 25° C. (Step 87). The reaction mixture is poured into ice water and the ether layer separated and dried. The ether is removed and the residue is chromatographed on silica gel.

[$^{123}$I]-1-Amino-3-(iodomethylenyl)cyclopentane-1-carboxylic acid 93

Aqueous 3% hydrogen peroxide is added to a mixture of sodium [$^{123}$I]iodide, tributylstannyl 91, and 0.1N HCl in a sealed vial protected by a charcoal vent (Step 88). The reaction is allowed to proceed for 30 min at ambient temperature, quenched with a solution of sodium bisulfite (300 mg/mL). Deprotection of 92 (Step 89) is achieved by using 1 mL of 4N HCl at 115° C. for 15 min and then the aqueous solution is passed through an ion-retardation resin (AG 11A8 50–100 mesh).

EXAMPLE 15

Synthesis of [$^{123}$I]-1-Amino-4-iodocyclohexane-1-carboxylic acid 94

[$^{123}$I]-Sodium iodide (10 mCi, 0.1N NaOH solution) will be dried by acetonitrile (2 mL) evaporation, the protected amino acid triflate 46 (3 mg) is introduced in an acetonitrile solution (1 mL). The (NCA) iodination reaction is performed at 85° C. for 5 min in a sealed vessel. Unreacted $^{123}$I is removed by diluting the reacting mixture with methylene chloride followed by passage through a silica gel Seppak which gives the $^{123}$I labeled product. Deprotection is achieved by using 1 mL of 4N HCl at 115° C. for 15 min and then the aqueous solution is passed through an ion-retardation resin (AG 11A8 50–100 mesh).

EXAMPLE 16

Synthesis of [$^{123}$I]-1-Amino-4-iodocyclohex-2-ene-1-carboxylic acid 1-t-Butyl carbamate-4-oxo-1-cyclohexane-1-carboxylic acid methyl ester 95

The protected alcohol 46 is added to a suspension of pyridinium chlorochromate in DMF at 25° C., stirred at 65° C. for 3 h, and then diluted with water (75 mL) (Step 77). The mixture is extracted with ether (2×50 mL) and the combined ether layers are washed with water, dried (MgSO4) and the solvent removed by roto-evaporation.

[1-t-Butyl carbamate-1-cyclohexane-1-carboxylic acid methyl ester] 4-hydrazone 96.

A mixture of hydrazine, the ketone 95, and 20 mL of ethanol is heated to boiling, and a drop of glacial acetic acid is added. The mixture is kept hot for 10 min (Step 78). The solution is cooled, and the hydrazone is collected by filtration.

[$^{123}$I]-1-Amino-4-iodo-cyclohex-2-ene-1-carboxylic acid 98

Aqueous 3% hydrogen peroxide is added to a mixture of sodium [$^{125}$I]iodide, hydrazone 96, and 0.1N HCl in a sealed vial protected by a charcoal vent (Step 79). The reaction is allowed to proceed for 30 min at ambient temperature, quenched with a solution of sodium bisulfite (300 mg/mL). Deprotection of 97 (Step 80) is achieved by using 1 mL of 4N HCl at 115° C. for 15 min and then the aqueous solution is passed through an ion-retardation resin (AG 11A8 50–100 mesh).

EXAMPLE 17

Synthesis of E-[$^{123}$I]-1-Amino-3-(2-iodoethenyl) cyclohexane-1-carboxylic acid 1-t-Butyl carbamate-4-bromo-1-cyclohexane-1-carboxylic acid methyl ester 99

Bromine is added to a mixture of alcohol 46 and triphenylphosphine in DMF at −10° C. (Step 81). After stirring for 1 h, the mixture is diluted with water and extracted with ether. The ether layer is washed with water, 10% sodium sulfite, and then dried. The ether is removed and the residue is chromatographed on silica gel.

1-t-Butyl carbamate-4-ethynyl-1-cyclohexane-1-carboxylic acid methyl ester 100

The bromo compound 99 in THF is added to a suspension of lithium acetylide ethylenediamne complex in THF stirred at 0° C. under a nitrogen atmosphere (Step 82). The mixture is stirred for 3 h at 25° C., poured into ice water, and extracted with ether. The ether extract is washed with ice cold 1N HCl, brine and then dried. The ether is removed and the residue is chromatographed on silica gel.

1-t-Butyl carbamate-4-((E)-2-tributylstannylethenyl)-1-cyclohexane-1-carboxylic acid methyl ester 101

Tributyltin hydride, the alkyne 100 and azobisisobutyronitrile are refluxed in toluene under nitrogen atmosphere for 10 h (Step 83). The reaction mixture is cooled, solvent removed in vacuo, and the residue chromatographed on silica gel.

[$^{123}$I]-1-Amino-4-((E)-2-iodoethenyl)cyclohexane-1-carboxylic acid 102

Aqueous 3% hydrogen peroxide is added to a mixture of sodium [$^{123}$I]iodide, tributylstannyl 101, and 0.1N HCl in a sealed vial protected by a charcoal vent (Step 84). The reaction is allowed to proceed for 30 min at ambient temperature, quenched with a solution of sodium bisulfite (300 mg/mL). Deprotection (Step 85) is achieved by using 1 mL of 4N HCl at 115° C. for 15 min and then the aqueous solution is passed through an ion-retardation resin (AG 11A8 50–100 mesh).

EXAMPLE 18

Synthesis of [$^{123}$I]-1-Amino-4-(iodomethylenyl) cyclohexane-1-carboxylic acid 1-t-Butyl carbamate-4-(bromomethylenyl)-1-cyclohexane-1-carboxylic acid methyl ester 103

The phosphonium salt 70 is suspended in ether and ethereal phenyllithium is added rapidly at 25° C. An orange-yellow solution results which becomes mustard yellow within 2 h. To this solution is added protected ketone 95 and the reaction mixture is heated at reflux for 8 h with stirring (Step 86). The ether is removed and the residue is chromatographed on silica gel.

1-t-Butyl carbamate-4-(tributylstannylmethylenyl)-1-cyclohexane-1-carboxylic acid methyl ester 104

To a solution of 103 in ether at −78° C. is added t-butyllithium (2 eq.) after 15 min tributyltin chloride is added and the mixture is warmed to 25° C. (Step 87). The reaction mixture is poured into ice water and the ether layer separated and dried. The ether is removed and the residue is chromatographed on silica gel.

[$^{123}$I]-1-Amino-4-(iodomethylenyl)cyclohexane-1-carboxylic acid 106

Aqueous 3% hydrogen peroxide will be added to a mixture of sodium [125I]iodide, tributylstannyl 104, and 0.1N HCl in a sealed vial protected by a charcoal vent (Step 88). The reaction is allowed to proceed for 30 min at ambient temperature, quenched with a solution of sodium bisulfite (300 mg/mL). Deprotection of 105 (Step 89) is achieved by using 1 mL of 4N HCl at 115° C. for 15 min and then the aqueous solution is passed through an ion-retardation resin (AG 11A8 50–100 mesh).

EXAMPLE 19

Biodistribution Studies in Tumor Bearing Rats

The distribution of radioactivity expressed as percent dose per gram in tissues of unfasted male fisher rats with implanted gliosarcoma at 5 min and 60 min after intravenous administration of [$^{18}$F]FACBC is shown in Table I. The initial level of accumulation of radioactivity in the brain after injection of [$^{18}$F]FACBC was low (0.11% dose/gram) at 5 min and increased slightly to 0.26% dose/gram. The agent, however, exhibited a high uptake in the brain tumor. The tumor uptake exhibited a maximum at 60 min (1.72% dose/gram) resulting in an increase of the tumor to brain ratio of 5.58 at 5 min to 6.61 at 60 min. The bone radioactivity showed no increase from 0.52% dose/gram at 5 min, to 0.38% dose/gram at 60 min, which demonstrates the expected stability of the 2-cyclobutyl group to significant in vivo defluorination.

We compared the tumor uptake of [$^{18}$F]FACBC with [$^{18}$F]2-FDG in a separate group of male fisher rats with implanted gliosarcoma at 5 min and 60 min after intravenous administration of [$^{18}$F]2-FDG the initial level of accumulation of radioactivity in the brain tumor after injection of [$^{18}$F]2-FDG was good, 1.29% dose/gram. The 2-FDG, however, exhibited a decrease in uptake in the brain tumor to 1.05% dose/gram at 60 min. The decrease of radioactivity in the tumor at 60 min in conjunction with initial high brain uptake and retention resulted in a low tumor to brain ratio of 0.84 at 60 min.

TABLE I

Distribution of Radioactivity in Tissues of Unfasted Male Fisher Rats following Intravenous Administration of [$^{18}$F]FACBC

| | Mean % Injected Dose/Gram (Average of 4 Rats) | |
|---|---|---|
| Organ | 5 min | 60 min |
| Blood | 0.58 | 0.32 |
| Heart | 0.70 | 0.56 |
| Muscle | 0.27 | 0.41 |
| Lung | 1.13 | 0.64 |
| Kidney | 1.08 | 0.60 |
| Spleen | 1.55 | 0.68 |
| Liver | 1.10 | 1.70 |
| Testis | 0.25 | 0.28 |
| Bone | 0.52 | 0.38 |
| Brain (B) | 0.11 | 0.26 |
| Tumor (T) | 0.61 | 1.72 |
| T/B | 5.58 | 6.61 |

This significant tumor to brain ratio of 6.6 at 60 min strongly supports the use of [$^{18}$F]FACBC as a valuable imaging agent for the diagnosis and management of treatment of metastatic disease in humans by PET.

We claim:
1. An amino acid analog having the general structure

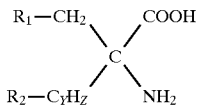

where $R_1$ is X, X—CH=CH—, or $R_3$
$R_2$ is H, or $R_3$ if $R_1$ is $R_3$,

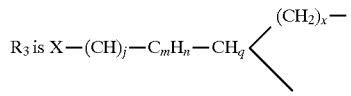

such that

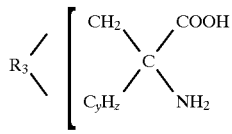

is formed
where x is 0 or 1,
y is 1 or 2,
z is 1, 2, 3 or 4 and z>y if y is 2,
q is 1 or 0 if n is 1 and j is 0,
n is 1 or 2, but 0 if m is 0,
m is 0 or 1,
j is 0 or 1, and
X is $^{18}F$, $^{123}I$, $^{125}I$, $^{131}I$, $^{75}Br$, $^{76}Br$, $^{77}Br$, or $^{82}Br$.
2. A compound of claim 1, wherein $R_1$ and $R_2=R_3$.
3. A cyclic compound according to claim 1 wherein
x is 0
y is 1
z is 2
q is 1
m is 0, and
j is 0.
4. A compound according to claim 3 wherein X is $^{18}F$, or $^{123}I$.
5. A compound according to claim 3 wherein X is $^{18}F$.
6. A compound according to claim 1 wherein $R_1$ and $R_2=R_3$,
x is 0 or 1
y is 2
z is 4
q is 1
m and j are each 0, and
X is $^{18}F$, or $^{123}I$.
7. A compound according to claim 6 wherein
x is 1
X is $^{18}F$.
8. The compound of claim 8 wherein x is 0 and X is $^{123}I$.
9. A compound according to claim 6 wherein x is 1 and X is $^{123}I$.
10. A compound according to claim 1
wherein $R_1$ and $R_2=R_3$
x is 0
y is 1
z is 2
q is 0
m is 1
n is 1
j is 0, and
X is $^{18}F$, or $^{123}I$.
11. A compound according to claim 10 wherein X is $^{18}F$.
12. A compound according to claim 1
wherein $R_1$ and $R_2=R_3$
x is 1
y is 1
z is 1
q is 0
m and j are 0, and
X is $^{18}F$, or $^{123}I$.
13. A compound according to claim 12 wherein X is $^{123}I$.
14. A compound according to claim 1
wherein $R_1$ and $R_2=R_3$
x is 0
y is 1
z is 2
q is 1
m is 1
n is 1
j is 1, and
X is $^{18}F$, or $^{123}I$.
15. The compound of claim 14 wherein X is $^{123}I$.
16. A compound according to claim 1
wherein $R_1$ and $R_2=R_3$
x is 0
y is 1
z is 2
q is 0
m is 0
j is 1, and
X is $^{18}F$, or $^{123}I$.
17. The compound of claim 16 wherein X is $^{123}I$.
18. A compound according to claim 1
wherein $R_1$ and $R_2=R_3$
x is 0 or 1
y is 2
z is 4
q is 1
m is 1
n is 1
j is 1, and
X is $^{18}F$, or $^{123}I$.
19. The compound of claim 18 wherein X is $^{18}F$.
20. The compound of claim 18 wherein X is $^{123}I$.
21. A compound according to claim 1
wherein $R_1$ and $R_2=R_3$
x is 0 or 1
y is 2
z is 4
q is 0
m is 0
j is 1, and
X is $^{18}F$, or $^{123}I$.
22. The compound of claim 21 wherein X is $^{18}F$.
23. The compound of claim 21 wherein X is $^{123}I$.
24. A compound of claim 1 wherein $R_1$ and $R_2 \neq R_3$.
25. A compound according to claim 24 wherein X is $^{18}F$.
26. A compound according to claim 1 wherein $R_1$ is X—CH=CH—, $R_2$ is H, y is 1 and z is 2.
27. A compound of claim 26 wherein X is $^{123}I$.

* * * * *

UNITED STATES PATENT AND TRADEMARK OFFICE
CERTIFICATE OF CORRECTION

PATENT NO. : 5,808,146

DATED : September 15, 1998

INVENTOR(S) : Goodman et al.

It is certified that error appears in the above-identified patent and that said Letters Patent is hereby corrected as shown below:

In the structure in Col. 6, line 64, delete "ClCH$_1$CH" and replace with --ClCH$_2$CH--.

In the structure described as Step 26 in Col. 13, line 55, delete "CO$_3$Et" and replace with --CO$_2$Et--.

In Col. 33, Claim 8, delete "claim 8" and replace with --claim 6--.

Signed and Sealed this

Fifteenth Day of December, 1998

Attest:

BRUCE LEHMAN

*Attesting Officer*    *Commissioner of Patents and Trademarks*

UNITED STATES PATENT AND TRADEMARK OFFICE
CERTIFICATE OF CORRECTION

| | |
|---|---|
| PATENT NO. | : 5,808,146 C1 |
| APPLICATION NO. | : 08/554906 |
| DATED | : January 2, 2007 |
| INVENTOR(S) | : Mark M. Goodman and Timothy Shoup |

It is certified that error appears in the above-identified patent and that said Letters Patent is hereby corrected as shown below:

On the title page, please change (73) Assignee to read --Emory University, Atlanta, Georgia.--

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,808,146 C1 | Page 1 of 1 |
| APPLICATION NO. | : 90/007810 | |
| DATED | : January 2, 2007 | |
| INVENTOR(S) | : Mark M. Goodman and Timothy Shoup | |

It is certified that error appears in the above-identified patent and that said Letters Patent is hereby corrected as shown below:

On the title page, please change (73) Assignee to read --Emory University, Atlanta, Georgia.--

This certificate supersedes Certificate of Correction issued May 22, 2007.

Signed and Sealed this

Twelfth Day of June, 2007

JON W. DUDAS
*Director of the United States Patent and Trademark Office*

(12) EX PARTE REEXAMINATION CERTIFICATE (5643rd)
United States Patent
Goodman et al.

(10) Number: US 5,808,146 C1
(45) Certificate Issued: Jan. 2, 2007

(54) AMINO ACID ANALOGS FOR TUMOR IMAGING

(75) Inventors: Mark M. Goodman, Atlanta, GA (US); Timothy Shoup, Decatur, GA (US)

(73) Assignee: U.S. Department of Energy, Washington, DC (US)

Reexamination Request:
No. 90/007,810, Nov. 22, 2005

Reexamination Certificate for:
Patent No.: 5,808,146
Issued: Sep. 15, 1998
Appl. No.: 08/554,906
Filed: Nov. 9, 1995

Certificate of Correction issued Dec. 15, 1998.

(51) Int. Cl.
*C07C 61/06* (2006.01)

(52) U.S. Cl. .................. 562/504; 562/505; 562/507; 562/574; 424/1.85; 424/1.89

(58) Field of Classification Search .................. None
See application file for complete search history.

(56) References Cited

PUBLICATIONS

Shoup, T. M. et al. (1995) "Synthesis and Evaluation of [18F]–1–amino–3–fluorocyclo–butane–1–carboxylic acid (FACBC) for Tumor Localization"; *Symposium Abstracts Eleventh International Symposium on Radiopharmaceutical Chemistry,* John Wiley & Sons, Ltd. pub.

*Primary Examiner*—Evelyn Mei Huang

(57) ABSTRACT

The invention provides novel amino acid compounds of use in detecting and evaluating brain and body tumors. These compounds combine the advantageous properties of 1-amino-cycloalkyl-1-carboxylic acids, namely, their rapid uptake and prolonged retention in tumors with the properties of halogen substituents, including certain useful halogen isotopes including fluorine-18, iodine-123, iodine-125, iodine-131, bromine-75, bromine-76, bromine-77 and bromine-82.

In one aspect, the invention features amino acid compounds that have a high specificity for target sites when administered to a subject in vivo. Preferred amino acid compounds show a target to non-target ratio of at least 5:1, are stable in vivo and substantially localized to target within 1 hour after administration. An especially preferred amino acid compound is $[^{18}F]$-1-amino-3-fluorocyclobutane-1-carboxylic acid (FACBC).

In another aspect, the invention features pharmaceutical compositions comprised of an α-amino acid moiety attached to either a four, five, or a six member carbon-chain ring. In addition, the invention features analogs of α-aminoisobutyric acid.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–27 is confirmed.

* * * * *